US009814703B2

(12) United States Patent
Beachy et al.

(10) Patent No.: US 9,814,703 B2
(45) Date of Patent: Nov. 14, 2017

(54) METHODS FOR TREATING CANCER BY ACTIVATION OF BMP SIGNALING

(71) Applicant: The Board of Trustees of the Leland Stanford Junior University, Stanford, CA (US)

(72) Inventors: Philip A. Beachy, Stanford, CA (US); Kunyoo Shin, Portland, OR (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 15/147,719

(22) PCT Filed: Nov. 13, 2014

(86) PCT No.: PCT/US2014/065486
§ 371 (c)(1),
(2) Date: May 5, 2016

(87) PCT Pub. No.: WO2015/073691
PCT Pub. Date: May 21, 2015

(65) Prior Publication Data
US 2017/0119740 A1 May 4, 2017

(51) Int. Cl.
*A01N 43/00* (2006.01)
*A61K 31/33* (2006.01)
*A61K 31/436* (2006.01)
*A61K 9/00* (2006.01)
*A61K 45/06* (2006.01)

(52) U.S. Cl.
CPC .......... *A61K 31/436* (2013.01); *A61K 9/0004* (2013.01); *A61K 9/0014* (2013.01); *A61K 9/0024* (2013.01); *A61K 31/33* (2013.01); *A61K 45/06* (2013.01)

(58) Field of Classification Search
CPC .................................................. A61K 31/395
USPC ....................................................... 514/183
See application file for complete search history.

(56) References Cited

U.S. PATENT DOCUMENTS

| | | |
|---|---|---|
| 4,894,366 A | 1/1990 | Okuhara et al. |
| 4,929,611 A | 5/1990 | Okuhara et al. |
| 4,956,352 A | 9/1990 | Okuhara et al. |
| 5,143,918 A | 9/1992 | Bochis et al. |
| 5,162,334 A | 11/1992 | Goulet et al. |
| 5,208,228 A | 5/1993 | Ok et al. |
| 5,208,241 A | 5/1993 | Ok et al. |
| 5,250,678 A | 10/1993 | Goulet et al. |
| 5,254,562 A | 10/1993 | Okuhara et al. |
| 5,262,533 A | 11/1993 | Sinclair et al. |
| 5,284,840 A | 2/1994 | Rupprecht et al. |
| 5,532,248 A | 7/1996 | Goulet et al. |
| 5,693,648 A | 12/1997 | Goulet et al. |
| 6,046,328 A | 4/2000 | Schonharting et al. |
| 6,613,798 B1 | 9/2003 | Porter et al. |
| 6,639,051 B2 | 10/2003 | Wang |
| 6,683,108 B1 | 1/2004 | Baxter et al. |
| 6,683,192 B2 | 1/2004 | Baxter et al. |
| 7,115,653 B2 | 10/2006 | Baxter et al. |
| 7,479,539 B1 | 1/2009 | Strauch et al. |
| 8,852,937 B2 | 10/2014 | Baxter et al. |
| 2002/0015702 A1 | 2/2002 | Burkly et al. |
| 2002/0198236 A1 | 12/2002 | Baxter et al. |
| 2003/0022819 A1 | 1/2003 | Ling et al. |
| 2003/0139457 A1 | 7/2003 | Baxter et al. |
| 2003/0166543 A1 | 9/2003 | Williams et al. |
| 2004/0077676 A1 | 4/2004 | Matsuoka et al. |
| 2004/0110663 A1 | 6/2004 | Dudek et al. |
| 2004/0126359 A1 | 7/2004 | Lamb et al. |
| 2005/0014796 A1 | 1/2005 | Baxter et al. |
| 2005/0054568 A1 | 3/2005 | Ling et al. |
| 2005/0070578 A1 | 3/2005 | Baxter et al. |
| 2005/0112125 A1 | 5/2005 | Burkly et al. |
| 2005/0256076 A1 | 11/2005 | Bumcrot |
| 2006/0160838 A1 | 7/2006 | Schlachter et al. |
| 2007/0110698 A1 | 5/2007 | Wang |
| 2007/0232661 A1 | 10/2007 | Beachy et al. |
| 2008/0058298 A1 | 3/2008 | Beachy et al. |
| 2008/0171328 A1 | 7/2008 | Tabin et al. |
| 2008/0207740 A1 | 8/2008 | Baxter et al. |
| 2009/0047212 A1 | 2/2009 | Berman et al. |
| 2009/0130091 A1 | 5/2009 | Beachy et al. |
| 2009/0156611 A1 | 6/2009 | Oinas et al. |
| 2010/0098624 A1 | 4/2010 | de Sauvage et al. |
| 2010/0183560 A1 | 7/2010 | Ling et al. |
| 2011/0190304 A1 | 8/2011 | Bastian et al. |
| 2011/0263602 A1 | 10/2011 | Bastian et al. |
| 2012/0148549 A1 | 6/2012 | Anderson et al. |
| 2012/0183603 A1 | 7/2012 | Beachy et al. |
| 2012/0238500 A1 | 9/2012 | Wang |
| 2012/0283258 A1 | 11/2012 | Guicherit et al. |
| 2012/0309730 A1 | 12/2012 | Parhami et al. |
| 2012/0316174 A1 | 12/2012 | Hipskind et al. |

(Continued)

OTHER PUBLICATIONS

Chang, et al., "BMP-4 Induction of Arrest and Differentiation of Osteoblast-Like Cells via p21CIP1 and p27KIP1 Regulation", Mol Endocrinol, 2009, 23(11):1827-1838.
Chen, et al., "Small molecule modulation of Smoothened activity", PNAS, 2002, 99(22):14071-14076.
Frank-Kamenetsky, et al., "Small-molecule modulators of Hedgehog signaling: identification and characterization of Smoothened agonists and antagonists", Journal of Biology, 2002, 1:10.
Gao, et al., "The BMP Inhibitor Coco Reactivates Breast Cancer Cells at Lung Metastatic sites", Cell, 2012, 150(4): 764-779.
Ishizuya-Oka, et al., "Shh/BMP-4 Signaling Pathway Is Essential for Intestinal Epithelial Development During Xenopus Larval-to-Adult Remodeling", Developmental Dynamics, 2006, 235:3240-3249.

(Continued)

*Primary Examiner* — Jeffrey H Murray
(74) *Attorney, Agent, or Firm* — James S. Keddie; Bozicevic, Field & Francis LLP

(57) ABSTRACT

Methods for treating cancer by activation of the Bmp pathway are disclosed. In particular, the invention relates to methods of treating cancer using agents that activate BMP signaling, e.g., FK506 (tacrolimus), to treat a subject for cancer.

14 Claims, 13 Drawing Sheets

(56) References Cited

U.S. PATENT DOCUMENTS

| | | |
|---|---|---|
| 2013/0011853 A1 | 1/2013 | Scales |
| 2013/0012513 A1 | 1/2013 | Vernier et al. |
| 2013/0035343 A1 | 2/2013 | Porta et al. |
| 2013/0085096 A1 | 4/2013 | Pepicelli et al. |
| 2013/0190350 A1 | 7/2013 | Rubin et al. |
| 2013/0230559 A1 | 9/2013 | Yoon et al. |
| 2013/0274233 A1 | 10/2013 | Wang et al. |
| 2013/0296333 A1 | 11/2013 | Cheng et al. |
| 2014/0018368 A1 | 1/2014 | Cai et al. |

OTHER PUBLICATIONS

Jiang, et al., "Hedgehog Signaling in Development and Cancer", Developmental Cell, 2008, 15(6):801-812.

Kim, et al., "Arsenic antagonizes the Hedgehog pathway by preventing ciliary accumulation and reducing stability of the Gli2 transcriptional effector", PNAS, 2010, 107(30): 13432-13437.

Kim, et al., "Itraconazole and arsenic trioxide inhibit hedgehog pathway activation and tumor growth associated with acquired resistance to smoothened antagonists", Cancer Cell, 2013, 23(1): 23-24.

Lee, et al., "Stromal response to Hedgehog signaling restrains pancreatic cancer progression", PNAS, 2014, 111(30): E3091-3100.

Mysorekar, et al., "Bone Morphogenetic Protein 4 Signaling Regulates Epithelial Renewal in the Urinary Tract in Response to Uropathogenic Infection", Cell Host & Microbe, 2009, 5: 463-475.

Paladini, et al., "Modulation of Hair Growth with Small Molecule Agonists of the Hedgehog Signaling Pathway", J Invest Dermatol, 2005, 125:638-646.

Petros, et al., "Conformation of two non-immunosuppressive FK506 analogs when bound to FKBP by isotope-filtered NMR", 1992 Federation of European Biochemical Societies, 1992, 308(3): 309-314.

Samanta, et al., "Interactions between ID and OLIG proteins mediate the inhibitory effects of BMP4 on oligodendroglial differentiation", Development, 2004, 131: 4131-4142.

Shin, et al., "Hedgehog Signaling Restrains Bladder Cancer Progression by Eliciting Stromal Production of Urothelial Differentiation Factors", Cancer Cell, 2014, 26: 521-533.

Sneddon, et al., "Bone morphogenetic protein antagonist gremlin 1 is widely expressed by cancer-associated stromal cells and can promote tumor cell proliferation", PNAS, 2006, 103(40): 14842-14847.

Zhu, et al., "BMP-FGF Signaling Axis Mediates Wnt-Induced Epidermal Stratification in Developing Mammalian Skin", PLOS Genetics, 2014, 10(10):e1004687.

FIG. 1A
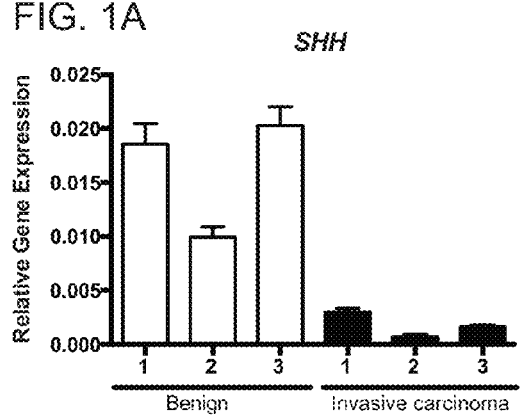
FIG. 1B
Immunohistochemistry for Shh
Benign human    Benign human (high mag)
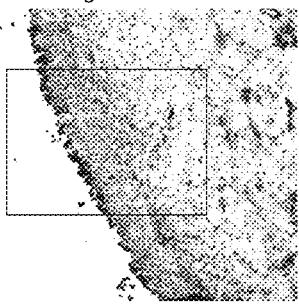 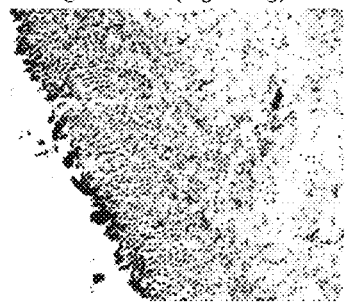
FIG. 1C
Immunohistochemistry for Shh
Human invasive carcinoma #4    Human invasive carcinoma #5
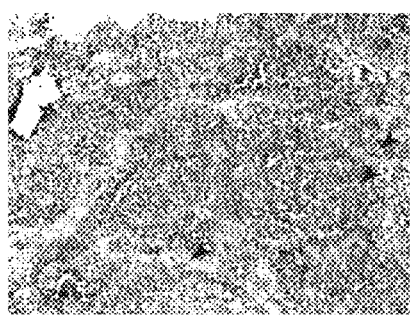 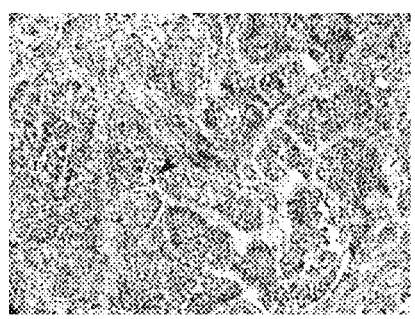
Human invasive carcinoma #6    Human invasive carcinoma #7
 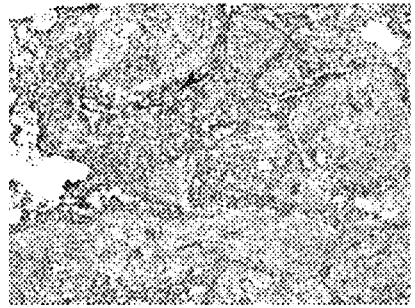

FIG. 5A
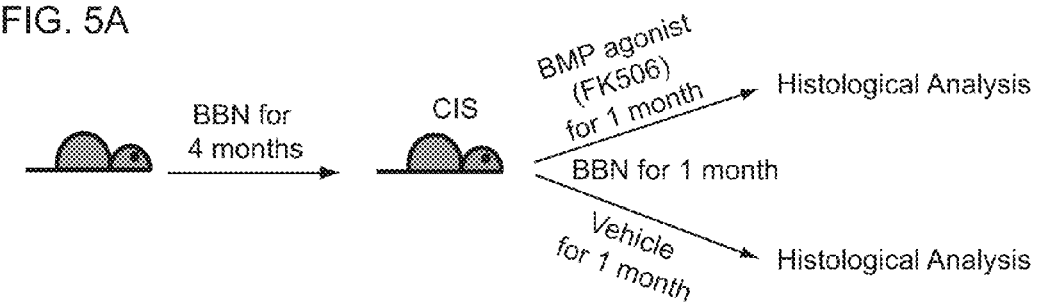
FIG. 5B
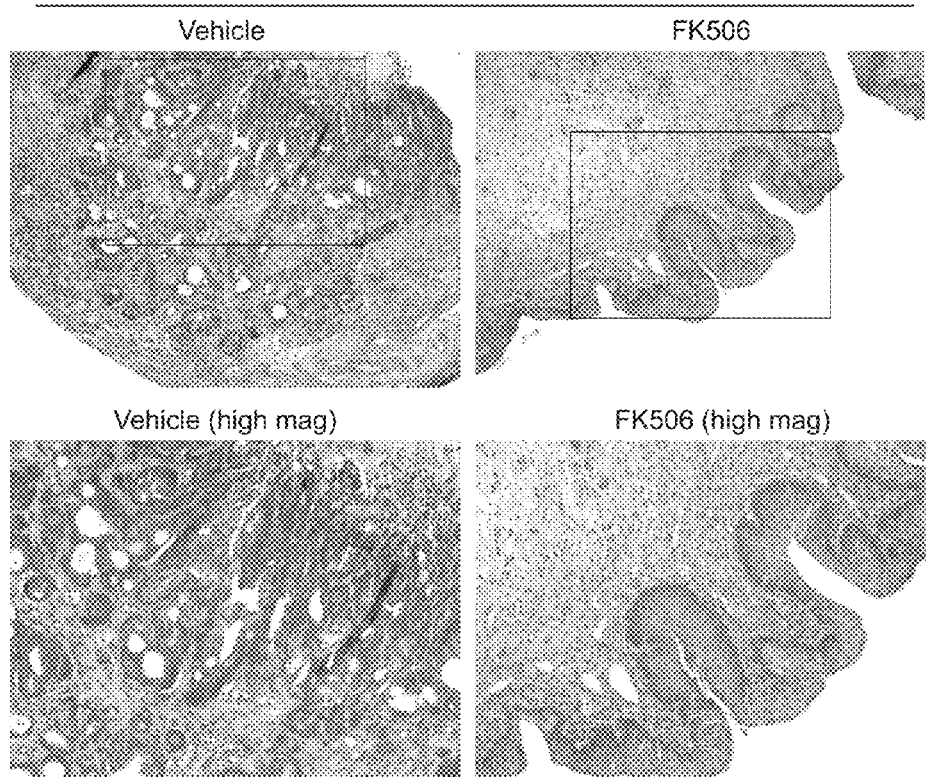
FIG. 5C
|  | Carcinogen treated | Drug | Starting/ending time of drug treatment | Total number of mice treated with drug | Number of mice that developed invasive tumors |
|---|---|---|---|---|---|
| Group 1 | BBN | Vehicle | 4mo/5mo | 9 | 7 |
| Group 2 | BBN | FK506 | 4mo/5mo | 10 | 0 |

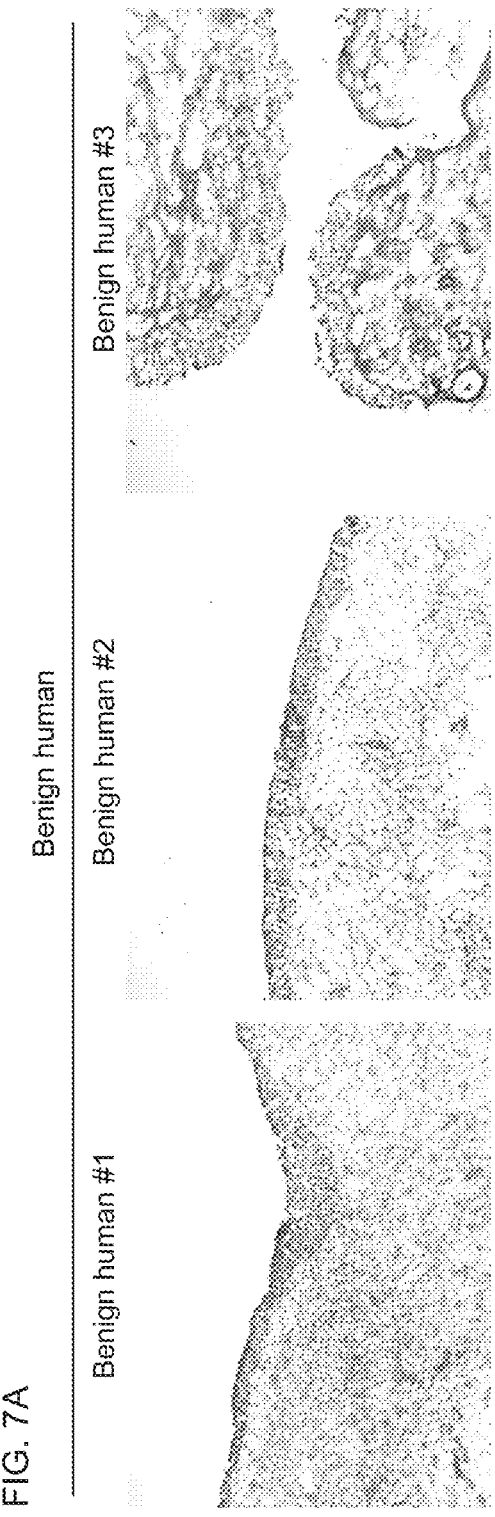
FIG. 7A  Benign human
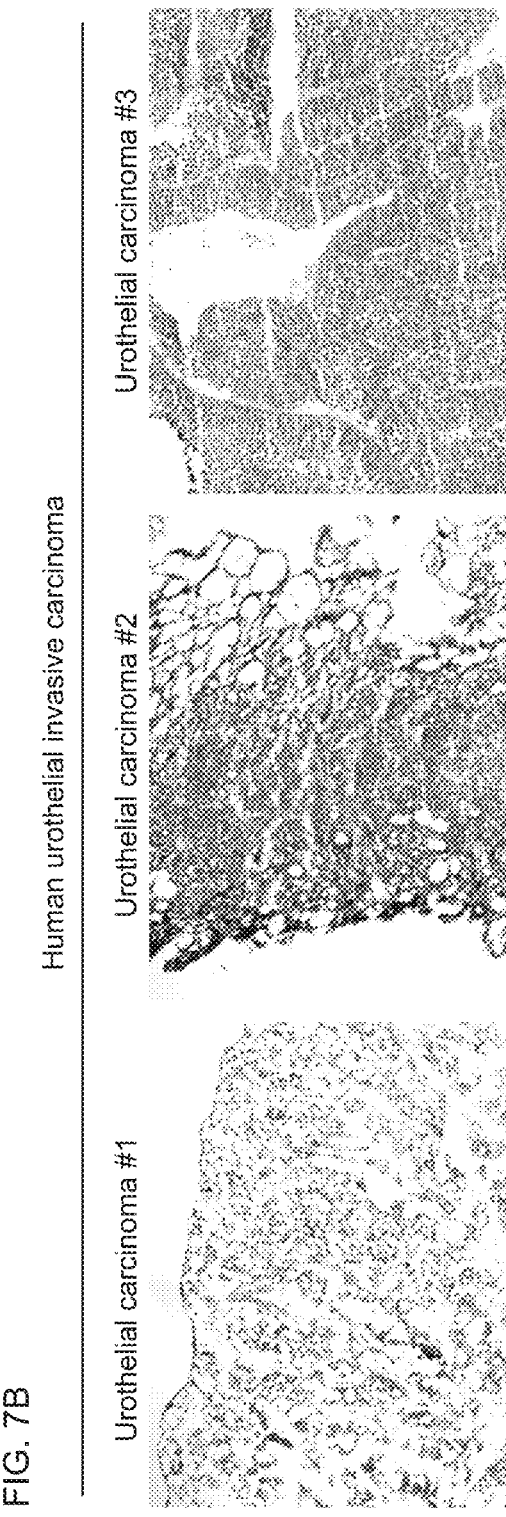
FIG. 7B  Human urothelial invasive carcinoma

FIG. 12

| Biological Process Term (Level 3) | Count | Percentage | p-value |
|---|---|---|---|
| GO:0006811: Ion transport | 26 | 8.099688474 | 5.08E-04 |
| GO:0050793: Regulation of developmental process | 21 | 6.542056075 | 1.80E-03 |
| GO:0030154: Cell differentiation | 42 | 13.08411215 | 3.61E-03 |
| GO:0007267: Cell-cell signaling | 13 | 4.049844237 | 4.25E-03 |
| GO:0006897: Endocytosis | 10 | 3.115264798 | 5.08E-03 |
| GO:0010324: Membrane invagination | 10 | 3.115264798 | 5.08E-03 |
| GO:0021537: Telencephalon development | 6 | 1.869158879 | 7.73E-03 |
| GO:0032879: Regulation of localization | 15 | 4.672897196 | 1.03E-02 |
| GO:0007010: Cytoskeleton organization | 13 | 4.049844237 | 1.04E-02 |
| GO:0048731: System development | 49 | 15.26479751 | 1.06E-02 |
| GO:0044262: Cellular carbohydrate metabolic process | 13 | 4.049844237 | 1.07E-02 |
| GO:0006810: Transport | 55 | 17.13395639 | 1.11E-02 |
| GO:0005975: Carbohydrate metabolic process | 16 | 4.984423676 | 1.12E-02 |
| GO:0005996: Monosaccharide metabolic process | 9 | 2.803738318 | 1.71E-02 |
| GO:0021549: Cerebellum development | 4 | 1.246105919 | 2.16E-02 |
| GO:0044057: Regulation of system process | 9 | 2.803738318 | 2.24E-02 |
| GO:0048513: Organ development | 40 | 12.46105919 | 2.45E-02 |
| GO:0009653: Anatomical structure morphogenesis | 29 | 9.034267913 | 2.53E-02 |
| GO:0051049: Regulation of transport | 11 | 3.426791277 | 2.54E-02 |
| GO:0051239: Regulation of multicellular organismal process | 22 | 6.853582555 | 2.57E-02 |
| GO:0007411: Axon guidance | 6 | 1.869158879 | 2.64E-02 |
| GO:0048522: Positive regulation of cellular process | 33 | 10.28037383 | 2.72E-02 |
| GO:0030902: Hindbrain development | 5 | 1.557632399 | 2.76E-02 |
| GO:0016192: Vesicle-mediated transport | 15 | 4.672897196 | 2.97E-02 |
| GO:0022037: Metencephalon development | 4 | 1.246105919 | 3.27E-02 |
| GO:0048518: Positive regulation of biological process | 36 | 11.21495327 | 3.28E-02 |
| GO:0045595: Regulation of cell differentiation | 13 | 4.049844237 | 3.38E-02 |
| GO:0031175: Neuron projection development | 9 | 2.803738318 | 3.41E-02 |
| GO:0048634: Regulation of muscle development | 4 | 1.246105919 | 3.69E-02 |
| GO:0051093: Negative regulation of developmental process | 9 | 2.803738318 | 4.08E-02 |

FIG. 13

| Accession No. | Symbol | Gene Name | Fold Change | p-value |
|---|---|---|---|---|
| NM_007555 | Bmp5 | Bone morphogenetic protein 5 | -8.0 | 1.59E-03 |
| NM_027852 | Rarres2 | Retinoic acid receptor responder (tazarotene induced) 2 | -6.5 | 1.31E-06 |
| NM_024406 | Fabp4 | Fatty acid binding protein 4 | -6.2 | 4.44E-03 |
| NM_009605 | Adipoq | Adiponectin, C1Q and collagen domain containing | -6.0 | 5.17E-05 |
| NM_007554 | Bmp4 | Bone morphogenetic protein 4 | -5.3 | 1.19E-04 |
| NM_177708 | Rtn4rl1 | Reticulon 4 receptor-like 1 | -5.0 | 4.92E-03 |
| NM_001164035 | Ntf3 | Neurotrophin 3 | -4.8 | 2.38E-03 |
| NM_009122 | Satb1 | Special AT-rich sequence binding protein 1 | -4.0 | 6.07E-03 |
| NM_031166 | Id4 | Inhibitor of DNA binding 4 | -3.8 | 8.97E-03 |
| NM_022984 | Retn | Resistin | -3.8 | 4.21E-03 |
| NM_025943 | Dzip1 | DAZ interacting protein 1 | -3.7 | 1.35E-03 |
| NM_173004 | Cntn4 | Contactin 4 | -3.6 | 4.23E-03 |
| NM_011255 | Rbp4 | Retinol binding protein 4, plasma | -3.6 | 8.99E-03 |
| NM_001001309 | Itga8 | Integrin alpha 8 | -3.6 | 1.11E-03 |
| NM_009204 | Slc2a4 | Solute carrier family 2 (facilitated glucose transporter), member 4 | -3.6 | 9.72E-03 |
| NM_009152 | Sema3a | Sema domain, immunoglobulin domain, short basic domain, secreted, (semaphorin) 3A | -3.4 | 5.00E-03 |
| NM_009365 | Tgfb1i1 | Transforming growth factor beta 1 induced transcript 1 | -3.4 | 1.75E-03 |
| NM_001111027 | Runx1t1 | Runt-related transcription factor 1; translocated to, 1 (cyclin D-related) | -3.4 | 2.46E-03 |
| NM_172621 | Clic5 | Chloride intracellular channel 5 | -3.4 | 1.91E-03 |
| NM_175260 | Myh10 | Myosin, heavy polypeptide 10, non-muscle | -3.2 | 6.48E-03 |
| NM_015753 | Zeb2 | Zinc finger E-box binding homeobox 2 | -3.1 | 2.77E-03 |
| NM_008086 | Gas1 | Growth arrest specific 1 | -3.1 | 8.17E-05 |
| NM_010681 | Lama4 | Laminin, alpha 4 | -3.1 | 3.14E-03 |
| NM_027280 | Nkd1 | Naked cuticle 1 homolog (Drosophila) | -3.1 | 7.01E-03 |
| NM_010518 | Igfbp5 | Insulin-like growth factor binding protein 5 | -3.0 | 3.68E-03 |
| NM_021339 | Cdon | Cell adhesion molecule-related/down-regulated by oncogenes | -2.9 | 3.60E-03 |
| NM_025282 | Mef2c | Myocyte enhancer factor 2C | -2.8 | 5.03E-03 |
| NM_010280 | Gfra3 | Glial cell line derived neurotrophic factor family receptor alpha 3 | -2.8 | 8.04E-04 |
| NM_177089 | Tacc1 | Transforming, acidic coiled-coil containing protein 1 | -2.7 | 2.76E-03 |
| NM_001081106 | Cytl1 | Cytokine-like 1 | -2.7 | 1.88E-04 |
| NM_001102400 | Dab2 | Disabled homolog 2 (Drosophila) | -2.7 | 4.71E-03 |
| NM_011614 | Tnfsf12 | Tumor necrosis factor (ligand) superfamily, member 12 | -2.6 | 2.49E-03 |
| NM_025891 | Smarcd3 | SWI/SNF related, matrix associated, actin dependent regulator of chromatin, subfamily d, member 3 | -2.6 | 8.69E-04 |
| NM_011129 | Sept4 | Septin 4 | -2.5 | 3.40E-03 |
| NM_001083334 | Bin1 | Bridging integrator 1 | -2.5 | 3.37E-03 |
| NM_009153 | Sema3b | Sema domain, immunoglobulin domain, short basic domain, secreted, (semaphorin) 3B | -2.2 | 4.37E-06 |
| NM_172506 | Boc | Biregional cell adhesion molecule-related/down-regulated by oncogenes (Cdon) binding protein | -2.2 | 7.64E-03 |
| NM_001159382 | Gjc1 | Gap junction protein, gamma 1 | -2.2 | 1.50E-03 |
| NM_023328 | Agtpbp1 | ATP/GTP binding protein 1 | -2.1 | 5.46E-03 |
| NM_008493 | Lep | Leptin | -2.1 | 6.27E-03 |
| NM_001085370 | Speg | SPEG complex locus | -2.1 | 9.46E-03 |
| NM_001198571 | Abi2 | Abl-interactor 2 | -2.0 | 4.28E-03 |

US 9,814,703 B2

METHODS FOR TREATING CANCER BY ACTIVATION OF BMP SIGNALING

GOVERNMENT RIGHTS

This invention was made with Government support under contract CA157877 awarded by the National Institutes of Health. The Government has certain rights in the invention.

TECHNICAL FIELD

The present invention pertains generally to methods of treating cancer. In particular, the invention relates to methods of treating cancer using an activator of the BMP pathway, such as FK506 (also known as tacrolimus).

BACKGROUND

Postnatal activity of Hedgehog signaling functions in regulation of stem cell physiology and tissue regeneration[1-5]. Following bacterial injury of the bladder, for example, Sonic hedgehog (Shh) produced in cells of the basal urothelium elicits production of factors from stromal cells, which in turn stimulate proliferation and differentiation of urothelial cells. This epithelial/stromal feedback leads to regeneration of the urothelium and restoration of its normal function[2]. In this regenerative response to murine urinary tract infection, the Shh-expressing basal cells function as stem cells by proliferating and supplying the progenitor cells that give rise to differentiated cells and ultimately replenish the injured urothelium[2].

These Shh-expressing basal stem cells also give rise to invasive urothelial carcinoma in a murine chemical carcinogenesis model utilizing the procarcinogen Nbutyl-N-4-hydroxybutyl nitrosamine (BBN)[6]. Marking of Shh-expressing basal cells in this model invariably marks tumors, whereas ablation of these cells decisively abrogates tumor formation. Surprisingly, although this combination of positive and negative evidence clearly demonstrates that basal urothelial stem cells expressing Shh are the exclusive cell of origin for invasive bladder cancer, expression of Shh is lost by the time invasive carcinomas are formed[6]. One possible explanation for this observation is that loss of Shh expression may somehow promote tumor progression. This effect, however, would represent a novel protective role for Hh pathway activity, as mutational activation of the Hh pathway is causative in the primary cells of basal cell carcinoma and medulloblastoma[7-9], and ligand-dependent pathway activity in stroma has been thought to promote growth of pancreatic cancer[10,11].

SUMMARY

Methods are provided for treating an individual having cancer. Aspects of the methods include activating the BMP signaling pathway in the subject. The invention relates to methods of treating cancer using an activator of the BMP pathway, such as FK506 (tacrolimus).

In one aspect, the invention includes a method of treating a subject for cancer, the method comprising administering a therapeutically effective amount of an agent that activates BMP signaling, e.g., FK506, to the subject. The methods of the invention can be used to treat various types of cancer including, but not limited to cancer of the bladder, lung, bronchi, trachea, esophagus, stomach, pancreas, liver, colon, rectum, breast, skin, or prostate. In one embodiment, the subject has urothelial cell carcinoma. In certain embodiments, low-dose FK506 therapy is used to avoid immunosuppression.

By "therapeutically effective dose or amount" of an agent that activates BMP signaling, e.g., FK506, is intended an amount that, when the agent that activates BMP signaling is administered as described herein, brings about a positive therapeutic response, such as an amount having anti-tumor activity. A positive therapeutic response may include preventing or delaying progression of a cancer to an invasive cancer. In certain embodiments, multiple cycles of the method of treatment can be administered to the subject for a time period sufficient to effect at least a partial tumor response, such as a time period of at least 6 months or at least 12 months. In one embodiment, the time period is sufficient to effect a complete tumor response.

In one aspect, the invention includes administration of a Hedgehog (Hh) pathway modulator, e.g., in concert or combination with an agent that activates BMP signaling. In one embodiment, an agent that activates BMP signaling is co-administered with a Hh antagonist. In another embodiment, an agent that activates BMP signaling is co-administered with a Hh agonist. These and other embodiments of the subject invention will readily occur to those of skill in the art in view of the disclosure herein.

Compositions and kits for practicing the methods of the disclosure are also provided. In some cases, a subject composition includes an agent that activates BMP signaling and an additional agent, e.g., an agent that inhibits Hh or inhibits Hh pathway signaling or an agent that activates Hh signaling.

BRIEF DESCRIPTION OF THE FIGURES

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIGS. 1A-1C. Absence of Shh expression in human invasive bladder carcinoma. FIG. 1A, SHH expression in benign urothelium and invasive urothelial carcinoma tissues. Data are presented as mean±s.e.m. FIG. 1B, FIG. 1B, Bladder sections were immunostained for Shh and counterstained with hematoxylin. FIG. 1B, The urothelial cells of a normal bladder are positive for Shh. The boxed area is shown enlarged on the right. FIG. 1C, Absence of Shh immunostaining in human invasive urothelial carcinoma from four different patients. Arrowheads indicate regions of Shh reactivity within tumor fibrovascular cores but absent in the lining carcinoma cells.

FIG. 2A, Mice were treated with tamoxifen (TM) prior to BBN exposure, and were exposed to BBN for 3 months. Bladder histology was analyzed by H&E. $Gli1^{CreER}$; $Smo^{flox/flox}$ mice developed invasive carcinoma by 3 months of BBN exposure (right panels show representative images) whereas $Gli1^{CreER}$; $Smo^{flox/WT}$ mice (left panels show representative images) did not. Lower panels show magnified views of the regions highlighted by boxes in upper panels. FIG. 2B, $Gli1^{CreER}$; or $Gli1^{CreER}$; $Smo^{flox/WT}$ mice were injected with TM and exposed to BBN until the animals died (n=10 in each group). Animals with homozygous loss of Smo function survived a median of 140 days, as compared to 215 days for Smo heterozygous control animals.

FIG. 3A, Comparison of the gene expression profiles revealed that 468 genes were down-regulated by at least 2-fold in $Gli1^{CreER}$; $Smo^{flox/flox}$ bladder samples (P<0.01). Gene ontology analysis indicated an enrichment of genes involved cell differentiation. Additional functional annotation of the down-regulated genes showed enrichment in the Swiss-Prot and Protein Information Resource Keywords (SP_PIR_KEYWORD) "Signal" and "Secreted". Venn diagram shows the number of overlapping genes in each of the three categories; 11 genes encode secreted proteins involved in cell signaling and differentiation. FIG. 3B, Expression of Gli1, Bmp4 and Bmp5 in tamoxifen-injected $Gli1^{CreER}$; $Smo^{flox/flox}$ and $Gli1^{CreER}$; $Smo^{flox/WT}$ mouse bladders following 2 months of BBN treatment. Expression of Gli1 (3.2 fold, P<0.0001), Bmp4 (16 fold, P<0.0001) and Bmp5 (34 fold, P<0.001) decreased in $Gli1^{CreER}$; $Smo^{flox/flox}$ bladders compared to $Gli1^{CreER}$; $Smo^{flox/WT}$ bladders. FIG. 3C, Bmp4 and Bmp5 expression in control bladders from wild-type mice with no BBN exposure, or bladders with invasive carcinoma from mice exposed to BBN for 6 months. Expression of Bmp4 (17 fold, P<0.001) and Bmp5 (60 fold, P<0.001) was decreased in invasive carcinoma samples as compared to control samples. Data are presented as mean±s.e.m., and significance was calculated by an unpaired Student's t-test.

FIG. 4A, FIG. 4B, GLI1, BMP4 and BMP5 expression in primary human bladder stromal or urothelial cells stimulated with ShhN protein or Hh pathway agonist SAG. FIG. 4A, Expression of GLI1 increased in cells treated with SAG (5.4 fold, P<0.001), and ShhN (1.6 fold, P<0.05), as compared to the unstimulated control (Ctrl), and this effect was reversed by addition of cyclopamine (Cyc). Urothelial cells did not respond to Hh pathway stimulation. FIG. 4B, Expression of BMP4 and BMP5 increased in cells treated with SAG (BMP4: 5.8 fold, P<0.001; BMP5: 2 fold, P<0.01), and ShhN (BMP4: 3.9 fold, P<0.001; BMP5: 1.6 fold, P<0.05), as compared to the unstimulated control (Ctrl), and this effect was reversed by the addition of cyclopamine FIG. 4C, Expression of BMP target genes ID4 (1.6 fold, P<0.01) and CDKN1B (2.4 fold, P<0.05) increased in urothelial cells treated with BMP agonist FK506 as compared to the DMSO control. FIG. 4D, Expression of BMP4 (11 fold, P<0.001) and BMP5 (7 fold, P<0.001) decreased in human invasive urothelial carcinoma compared to benign bladder tissues. Data are presented as mean±s.e.m., and significance was calculated by an unpaired Student's t-test.

FIGS. 5A-5C. Pharmacological activation of Bmp signaling in vivo impedes tumor progression.

FIG. 5A, Schematic diagram illustrating the experimental strategies used to analyze the effect of Bmp pathway activation on bladder cancer progression. Mice were exposed to BBN for 4 months, and then treated with the BMP agonist FK506 or a vehicle control for a month with continued BBN exposure before histopathological analysis of the bladders. FIG. 5B, Hematoxylin and eosin (H&E) stained bladder sections from mice exposed to BBN for 5 months with 1 month of treatment with FK506 or a vehicle control. Lower panels show magnified views of the regions highlighted by boxes in upper panels. FIG. 5C, Table summarizing the results obtained from the treatment of mice exposed to BBN with FK506 or a vehicle control.

FIGS. 7A-7B. Histological analysis of bladder specimens used for gene expression analyses. FIG. 7A, Hematoxylin and eosin (H&E) stained sections from three benign human bladder samples used for gene expression analyses. FIG. 7B, H&E stained sections from three human invasive urothelial carcinoma samples used for gene expression analyses.

FIG. 8A, Validation of the anti-Shh antibody used for immunohistochemistry. The anti-Shh antibody specifically labels the floor plate and notochord in a section of an E10.5 mouse embryo. FIG. 8B, One benign human bladder urothelium, and three patient-derived muscle-invasive urothelial carcinoma samples were immunostained for Shh and counterstained with hematoxylin.

FIG. 9A, Schematic diagram illustrating the experimental strategies for FIGS. 2A-2B and FIGS. 3A-3C. $Gli1^{CreER}$; $Smo^{flox/flox}$ and $Gli1^{CreER}$; $Smo^{flox/WT}$ mice injected with TM on three consecutive days were treated with BBN for 2 or 3 months, and the bladders harvested for microarray gene expression analysis (detailed in FIGS. 3A-3C) or histological analysis by H&E staining (detailed in FIGS. 2A-2B) respectively. FIG. 9B, Expression of Uroplakins, indicative of urothelial differentiation, was significantly decreased in Smo-ablated bladders.

FIG. 12 provides Table 1. Gene ontology analysis of genes down-regulated in $Gli1^{CreER}$; $Smo^{flox/flox}$ mouse bladders following 2 months of BBN treatment.

FIG. 13 provides Table 2. Genes down-regulated in $Gli1^{CreER}$; $Smo^{flox/flox}$ mouse bladders, following 2 months of BBN treatment, involved in cell differentiation (GO: 0030154).

DETAILED DESCRIPTION OF THE EMBODIMENTS

Figure 2A:
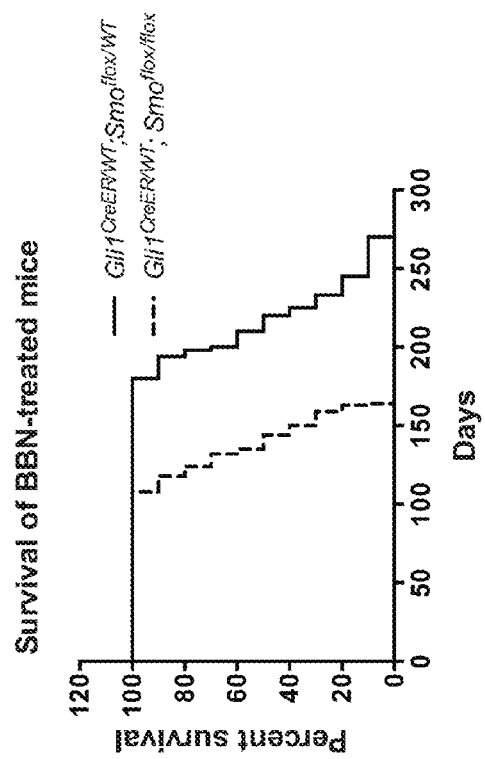
FIGS. 2A-2B. Genetic ablation of Hh response accelerate bladder carcinogenesis.

The practice of the present invention will employ, unless otherwise indicated, conventional methods of pharmacology, chemistry, biochemistry, recombinant DNA techniques and immunology, within the skill of the art. Such techniques are explained fully in the literature. See, e.g., *Handbook of Experimental Immunology*, Vols. I-IV (D. M. Weir and C. C.

Blackwell eds., Blackwell Scientific Publications); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.).

All publications, patents and patent applications cited herein, whether supra or infra, are hereby incorporated by reference in their entireties.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed Definitions In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "an agonist" includes a mixture of two or more such agonists, and the like.

By "anti-tumor activity" is intended a reduction in the rate of cell proliferation, and hence a decline in growth rate of an existing tumor or in a tumor that arises during therapy, and/or destruction of existing neoplastic (tumor) cells or newly formed neoplastic cells, and hence a decrease in the overall size of a tumor during therapy.

A "therapeutically effective dose" or "therapeutic dose" is an amount sufficient to effect desired clinical results (i.e., achieve therapeutic efficacy). For example, a therapeutically effective dose or amount of FK506 is intended to be an amount that, when the FK506 is administered as described herein, brings about a positive therapeutic response, such as an amount having anti-tumor activity. A positive therapeutic response may include preventing or delaying progression of carcinoma-in-situ to invasive carcinoma. A therapeutically effective dose can be administered in one or more administrations. For purposes of this disclosure, a therapeutically effective dose of an activator of BMP signaling (e.g., FK506, and the like) and/or compositions (e.g., compositions that include an activator of BMP signaling) is an amount that is sufficient, when administered to the individual, to palliate, ameliorate, stabilize, reverse, prevent, slow or delay the progression of the disease state (e.g., cancer, tumor, etc.) by, for example, inducing BMP signaling.

The term "tumor response" as used herein means a reduction or elimination of all measurable lesions. The criteria for tumor response are based on the WHO Reporting Criteria [WHO Offset Publication, 48-World Health Organization, Geneva, Switzerland, (1979)]. Ideally, all uni- or bidimensionally measurable lesions should be measured at each assessment. When multiple lesions are present in any organ, such measurements may not be possible and, under such circumstances, up to 6 representative lesions should be selected, if available.

The term "complete response" (CR) as used herein means a complete disappearance of all clinically detectable malignant disease. CR may be determined by two or more consecutive assessments in which malignant disease is not clinically detectable, including e.g., 2, 3, 4, 5, 6, 7, 8, 9, 10, or more assessments. Such assessments may, in some instances, be separated by a length of time as determined to be necessary by a clinician, e.g., to add confidence to the determination of CR, including, e.g., a week, 2 weeks, 3, weeks, 4 weeks, 5, weeks, 6 weeks, 7 weeks, two months, three months, four months, five months, six months, seven months, eight months, nine months, ten months, eleven months, a year, two years, three years, four years, five years, or more. For example, CR may be determined by 2 assessments at least 4 weeks apart.

The term "partial response" (PR) as used herein means a measurable reduction in the clinically detectable malignant disease. Any convenient measure or assessment of the clinically detectable disease may be employed for determining PR. Such convenient measures will vary and, in some instances, may include direct measurement of the disease, e.g., direct measurement of size of a tumor or direct measurement of the number of cancerous lesions, etc. PR may be determined by two or more consecutive assessments in which malignant disease is measurably decreased in the latter measurement(s), e.g., as compared to baseline or as compared to the previous measurement. The number of assessments used in making a determination of PR will vary and may include 2 or more, including e.g., 2, 3, 4, 5, 6, 7, 8, 9, 10, or more assessments. Such assessments may, in some instances, be separated by a length of time as determined to be necessary by a clinician, e.g., to add confidence to the determination of PR, including, e.g., a week, 2 weeks, 3, weeks, 4 weeks, 5, weeks, 6 weeks, 7 weeks, two months, three months, four months, five months, six months, seven months, eight months, nine months, ten months, eleven months, a year, two years, three years, four years, five years, or more. In some instances, a PR may be determined based on a measurable reduction in the clinically detectable malignant disease of 5% or more, including but not limited to, e.g., 10% or more, 15% or more, 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, or 95% or more. A determination of PR may also include an assessment of a lack of disease progression and/or a lack of any indication of new disease, e.g., metastatic disease occurring at a site different from the primary disease. For example, in some instances, PR may be determined based on a 50% or more measurable reduction from baseline in the sum of the products of the longest perpendicular diameters of all measurable disease without progression of evaluable disease and without evidence of any new lesions as determined by at least two consecutive assessments at least four weeks apart. Such assessments used in determining PR, in some instances, should show a partial decrease in the size of lytic lesions, recalcifications of lytic lesions, or decreased density of blastic lesions.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, camels, etc. In some embodiments, the mammal is human. In some cases, the methods of the invention find use in experimental animals, in veterinary application, and in the development of animal models, including, but not limited to, rodents including mice, rats, and hamsters; and primates.

The terms "specific binding," "specifically binds," and the like, refer to non-covalent or covalent preferential binding to a molecule relative to other molecules or moieties in a solution or reaction mixture (e.g., an antibody specifically binds to a particular polypeptide or epitope relative to other available polypeptides). In some embodiments, the affinity of one molecule for another molecule to which it specifically binds is characterized by a $K_D$ (dissociation constant) of $10^{-5}$ M or less (e.g., $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, or $10^{-16}$ M or less). "Affinity" refers to the strength of binding, increased binding affinity being correlated with a lower $K_D$.

The term "specific binding member" as used herein refers to a member of a specific binding pair (i.e., two molecules, usually two different molecules, where one of the molecules, e.g., a first specific binding member, through non-covalent means specifically binds to the other molecule, e.g., a second specific binding member).

The term "specific binding agent" as used herein refers to any agent that specifically binds a biomolecule (e.g., a protein, a peptide, a ligand, a receptor, etc.). In some cases, a "specific binding agent" for a repressor of BMP signaling (e.g., an agent that specifically binds to and inhibits a biomolecule that represses BMP signaling) is used. Specific binding agents can be any type of molecule. In some cases, a specific binding agent is an antibody or a fragment thereof. In some cases, a specific binding agent is small molecule (e.g., a macrolide, e.g., FK506; and the like)

MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

The present invention is based on the discovery of a novel therapeutic methodology for effectively treating cancer. The methods utilize activators of BMP signaling, e.g., FK506 (also known as tacrolimus). Without being bound by a particular theory, activation of the Bmp pathway has been shown to stimulate urothelial differentiation and impede tumor progression. For example, the inventors have shown that urothelial progression to invasive carcinoma is dramatically reduced using FK506 (see Example 1).

In order to further an understanding of the invention, a more detailed discussion is provided below regarding methods for treating cancer with an agent that activates BMP signaling.

In some instances, treatment of a subject having cancer as described herein includes administering to the subject an effective amount of an agent that activates BMP signaling, e.g., by specifically binding to a member of the BMP signaling pathway or a related pathway that signals through the BMP signaling pathway. In some embodiments, the agent that activates BMP signaling specifically binds to a repressor of BMP signaling and inhibits the function of the BMP repressor.

Repressors of BMP signaling, also known as negative regulators of BMP signaling, may vary and in some cases may refer to those molecules that hold in an inactive state or conformation components of the BMP signaling pathway or components of related pathways that influence the BMP signaling pathway. For example, a repressor of the BMP signaling pathway may be a molecule that specifically binds to and holds in an inactive confirmation a serine/threonine kinase receptor, including e.g., a type I serine/threonine kinase receptor, a type II serine/threonine kinase receptor, etc., including e.g., BMP receptors, TFG-β receptors, and the like. Negative regulators of BMP signaling include but are not limited to, e.g., those human and mouse proteins identified by the gene ontology term GO:0030514 which includes UniProtKB IDs: A0A024R1Y8 (FSTL3, Follistatin-like 3 (Secreted glycoprotein), isoform CRA_a), A0A024R316 (WNT5A, Protein Wnt), A0A024R3Y1 (hCG_1643547, HCG1643547, isoform CRA_a), A0A024RA82 (hCG_37272, HCG37272, isoform CRA_b), A0A024RDV9 (SPG20, Spastic paraplegia 20, spartin (Troyer syndrome), isoform CRA_a), A2ADM9 (Cer1, Cerberus 1 homolog (*Xenopus laevis*)), A2AV23 (Abl1, Tyrosine-protein kinase ABL1), A2CG33 (Chrd, Chordin), A2RS90 (Nanog, MCG132219), A2RTJ4 (Nog, Noggin), A4D125 (SOSTDC1, Sclerostin domain containing 1), A6H5Z6 (Chrd, Chordin), A6XAA7 (GREM1, Gremlin 1, cysteine knot superfamily, homolog (*Xenopus laevis*), isoform CRA_b), A7M7C7 (Skor2, SKI family transcriptional corepressor 2), A8K224 (cDNA FLJ35157 fis, clone PLACE6011156, highly similar to Serine protease HTRA1 (EC 3.4.21.-)), A8KAM5 (cDNA FLJ77519, highly similar to *Homo sapiens* secreted frizzled related protein mRNA), B1AUF1 (Ski, Ski oncogene), B1AUF2 (Ski, Ski oncogene), B2RPW6 (Smad7, Mothers against decapentaplegic homolog), B2RQA5 (Sost, Sclerostin), B2RUY7 (VWC2L, von Willebrand factor C domain-containing protein 2-like), B3KRU6 (cDNA FLJ34926 fis, clone NT2RP7003319, highly similar to Chordin-like protein 1), B3KSM5 (cDNA FLJ36603 fis, clone TRACH2015180, highly similar to Secreted frizzled-related protein 2), B7ZN41 (Nanog, Nanog protein), C6ZRK4 (TCF7L2 isoform pFC8A_TCF7L2_H2_ex3-11-12-13-14), D3YV59 (Chrdl2, Chordin-like protein 2), D3YWT3 (Tcf712, Transcription factor 7-like 2), D3YX64 (Skor1, Ladybird homeobox 1 homolog (Drosophila) corepressor 1, isoform CRA_b), D3Z002 (Tcf712, Transcription factor 7-like 2), D3Z0J2 (Cav1, Caveolin), D3Z1L0 (Tcf712, Transcription factor 7-like 2), D3Z1M5 (Spg20, Spartin), D3Z2D6 (Spg20, Spartin), D3Z2K5 (Tcf712, Transcription factor 7-like 2), D3Z3F8 (Spg20, Spartin), E9Q990 (Tcf712, Transcription factor 7-like 2), E9QP19 (Trim33, E3 ubiquitin-protein ligase TRIM33), E9QP59 (Lemd3, Inner nuclear membrane protein Mani), E9QQ89 (Tcf712, Transcription factor 7-like 2), E9QQ90 (Tcf712, Transcription factor 7-like 2), E9QQ91 (Tcf712, Transcription factor 7-like 2), F5GZI2 (NANOG, Homeobox protein NANOG), F6WCT1 (Chrdl2, Chordin-like protein 2), F6WPX2 (Tcf712, Transcription factor 7-like 2), F6XQR1 (Tcf712, Transcription factor 7-like 2), G3UX42 (Smad7, Mothers against decapentaplegic homolog 7), G3UXH8 (Smad7, Mothers against decapentaplegic homolog 7), G3V3E1 (SKOR1, SKI family transcriptional corepressor 1), G3V5H7 (SKOR1, SKI family transcriptional corepressor 1), H0Y7G9 (HTRA1, Serine protease HTRA1), H9CXX2 (NOTCH1, Notch 1), I1W660 (DKK1, Dickkopf-like protein 1), J7H4F6 (NANOG, NANOG), K7EKF0 (SMAD7, Mothers against decapentaplegic homolog 7), O15105 (SMAD7, Mothers against decapentaplegic homolog 7), O35182 (Smad6, Mothers against decapentaplegic homolog 6), O35253 (Smad7, Mothers against decapentaplegic homolog 7), O43541 (SMAD6, Mothers against decapentaplegic homolog 6), O54908 (Dkk1, Dickkopf-related protein 1), O55233 (Cer1, Cerberus), O60565 (GREM1, Gremlin-1), O70326 (Grem1, Gremlin-1), O70421 (Fzd1, Frizzled-1), O88273 (Grem2, Gremlin-2), O94907 (DKK1, Dickkopf-related protein 1), O95633 (FSTL3, Follistatin-related protein 3), O95813 (CER1, Cerberus), P00520 (Abl1, Tyrosine-protein kinase ABL1), PO4426 (Wnt1, Proto-oncogene Wnt-1), PO4628 (WNT1, Proto-oncogene Wnt-1), P12755 (SKI, Ski oncogene), P22725 (Wnt5a, Protein Wnt-5a), P35555 (FBN1, Fibrillin-1), P41221 (WNTSA, Protein Wnt-5a), P41271 (NBL1, Neuroblastoma suppressor of tumorigenicity 1), P46531 (NOTCH1, Neurogenic locus notch homolog protein 1), P49817 (Cav1, Caveolin-1), P50616 (TOB1, Protein Tob1), P83110 (HTRA3, Serine protease HTRA3), P84550 (SKOR1, SKI family transcriptional corepressor 1), P97299 (Sfrp2, Secreted frizzled-related protein 2), P97466 (Nog, Noggin), Q01705 (Notch1, Neurogenic locus notch homolog protein 1), Q03135 (CAV1, Caveolin-1), Q07104 (Gdf3, Growth/differentiation factor 3), Q13253 (NOG, Noggin), Q2TAL6 (VWC2, Brorin), Q3SYK5 (Abl1, Abl1 protein), Q3TM13 (Abl1, Putative uncharacterized protein), Q3TNY7 (Grem1, MCG19184), Q3TP73 (Chrdl1, Chordin-like 1, isoform CRA_c), Q3TVW1 (Spg20, Spastic paraplegia 20, spartin (Troyer syndrome) homolog (Human), isoform CRA_b), Q3UENO (Chrd, Putative uncharacterized protein), Q3UI35 (Sfrp2, Secreted frizzled-related protein 2), Q3UQ91 (Tob1, Putative uncharacterized protein), Q3UR96 (Wnt1, Protein Wnt), Q3UUM9 (Sfrp2, Putative uncharacterized protein), Q3UY25 (Grem1, Putative uncharacterized protein), Q3V1G9 (Tcf712, Transcription factor 7-like 2), Q3V2W1 (Abl1, Putative uncharacterized protein), Q505H4 (Vwc21, von Willebrand factor C domain-containing protein 2-like), Q542M9 (Fst13, Follistatin-like 3), Q59FB2 (Chordin-like 1 variant), Q5DU60 (Chrd, MFLJ00220 protein), Q5TM83 (Nanog, Homeobox protein NANOG), Q60698 (Ski, Ski oncogene), Q61262 (Abl1, Putative uncharacterized protein), Q61471 (Tob1, Protein Tob1), Q61477 (Nbl1, Neuroblastoma suppressor of tumorigenicity 1), Q61554 (Fbn1, Fibrillin-1), Q6FHW4 (TCF7L2, Transcription factor 7-like 2 (T-cell specific, HMG-box), isoform CRA_e), Q6NV61 (Ski, Ski protein), Q6NXY0 (Chrdl1, Chrdl1 protein), Q6X4U4 (SOSTDC1, Sclerostin domain-containing protein 1), Q76LW6 (Dandy, DAN domain family member 5), Q7TQ32 (Hfe2, Hemojuvelin), Q7Z459 (SKI, Ski oncoprotein), Q7Z461 (SKI, Ski oncoprotein), Q7Z462 (SKI, Ski oncoprotein), Q8OWT9 (Tcf712, Transcription factor 7-like 2), Q80Z64 (Nanog, Homeobox protein NANOG), Q8BJD6 (Fst13, Putative uncharacterized protein), Q8BS68 (Tcf712, Putative uncharacterized protein), Q8BX46 (Skor1, SKI family transcriptional corepressor 1), Q8C4U3 (Sfrp1, Secreted frizzled-related protein 1), Q8C8N3 (Vwc2, Brorin), Q8CAI6 (Tcf712, Putative uncharacterized protein), Q8CAT4 (Abl1, Putative uncharacterized protein), Q8CJ69 (Bmper, BMP-binding endothelial regulator protein), Q8KOR3 (Ski, Ski protein), Q8NOX7 (SPG20, Spartin), Q8N2W7 (Putative uncharacterized protein), Q8N474 (SFRP1, Secreted frizzled-related protein 1), Q8N8U9 (BMPER, BMP-binding endothelial regulator protein), Q8N907 (DAND5, DAN domain family member 5), Q8R1X6 (Spg20, Spartin), Q8VEA6 (Chrdl2, Chordin-like protein 2), Q91V65 (wnt-1, Protein Wnt), Q920C1 (Chrdl1, Chordin-like protein 1), Q924A0 (Tcf712, Transcription factor 7-like 2), Q92743 (HTRA1, Serine protease HTRA1), Q96HF1 (SFRP2, Secreted frizzled-related protein 2), Q99KU4 (Ski, Ski protein), Q99P68 (Sost, Sclerostin), Q99PP7 (Trim33, E3 ubiquitin-protein ligase TRIM33), Q9BQB4 (SOST, Sclerostin), Q9BU40 (CHRDL1, Chordin-like protein 1), Q9BZZ6 (FRP1, Frizzled-related protein), Q9CQN4 (Sostdc1, Sclerostin domain-containing protein 1), Q9CTE9 (Ski, Putative uncharacterized protein), Q9D236 (Htra3, Serine protease HTRA3), Q9DBIO (Tmprss6, Transmembrane protease serine 6), Q9EP52 (Twsg1, Twisted gastrulation protein homolog 1), Q9EQC7 (Fst13, Follistatin-related protein 3), Q9GZX9 (TWSG1, Twisted gastrulation protein homolog 1), Q9H2X0 (CHRD, Chordin), Q9H2X6 (HIPK2, Homeodomain-interacting protein kinase 2), Q9H772 (GREM2, Gremlin-2), Q9H9S0 (NANOG, Homeobox protein NANOG), Q9HCE7 (SMURF1, E3 ubiquitin-protein ligase SMURF1), Q9NQB0 (TCF7L2, Transcription factor 7-like 2), Q9NR23 (GDF3, Growth/differentiation factor 3), Q9QZR5 (Hipk2, Homeodomain-interacting protein kinase 2), Q9R118 (Htra1, Serine protease HTRA1), Q9UP38 (FZD1, Frizzled-1), Q9UPN9 (TRIM33, E3 ubiquitin-protein ligase TRIM33), Q9Y2U8 (LEMD3, Inner nuclear membrane protein Mani), Q9ZOE2 (Chrd, Chordin), S4R1K6 (Chrd, Chordin), W5VTTO (Notch 1), and the like.

Negative regulators of BMP signaling may, in some instances, include, e.g., those human and mouse proteins identified by the gene ontology term GO:0030512 as negative regulators of TGF-β receptor signaling pathway, which includes UniProtKB IDs: A0A024RBLO (CHST11, Carbohydrate (Chondroitin 4) sulfotransferase 11, isoform CRA_a), A0A087X0E6 (SKOR2, SKI family transcriptional corepressor 2), A1A5B7 (Adamts12, ADAMTS-like 2), A2A929 (Prdm16, PR domain zinc finger protein 16), A2A930 (Prdm16, PR domain zinc finger protein 16), A2A931 (Prdm16, PR domain zinc finger protein 16), A2A933 (Prdm16, PR domain zinc finger protein 16), A2A934 (Prdm16, PR domain zinc finger protein 16), A2A935 (Prdm16, PR domain zinc finger protein 16), A219Z0 (TP53, p53), A2I9Z1 (TP53, Tumor protein p53), A4GW67 (TP53, Cellular tumor antigen p53), A4GW74 (TP53, Cellular tumor antigen p53), A4GW75 (TP53, Cellular tumor antigen p53), A4GW76 (TP53, Cellular tumor antigen p53), A4GW97 (TP53, Cellular tumor antigen p53), A4GWB5 (TP53, Cellular tumor antigen p53), A4GWB8 (TP53, Tumor protein p53), A4GWD0 (TP53, Tumor protein p53), A5YM40 (TGFB3, TGFB3 protein), A6H6K1 (Aspn, Asporin), A6MDD3 (Cd109, CD109 antigen, isoform CRA_a), A7M7C7 (Skor2, SKI family transcriptional corepressor 2), A8K224 (cDNA FLJ35157 fis, clone PLACE6011156, highly similar to Serine protease HTRA1 (EC 3.4.21.-)), B0AZV0 (cDNA, FLJ79540, highly similar to Serine-threonine kinase receptor-associatedprotein), B1AUF1 (Ski, Ski oncogene), B1AUF2 (Ski, Ski oncogene), B2CNW3 (ONECUT1, One cut homeobox 1), B2RPW6 (Smad7, Mothers against decapentaplegic homolog), B2RUC7 (Strap, Serine/threonine kinase receptor associated protein), B3KTI8 (cDNA FI138342 fis, clone FCBBF3028188, highly similar to Homo sapiens sorting nexin 25 (SNX25), mRNA), B4DNI2 (Cellular tumor antigen p53), B5AKF6 (TP53, Mutant p53 tumor suppressor), B7ZMT9 (Chstl1, Uncharacterized protein), B9EHC3 (Chstl1, Carbohydrate sulfotransferase 11), C9J8R9 (SKIL, Ski-like protein), D3YX64 (Skor1, Ladybird homeobox 1 homolog (Drosophila) corepressor 1, isoform CRA_b), D3YYG2 (Ski1, Ski-like protein), D3Z147 (Cav2, Caveolin-2), D3Z7C5 (Ski1, Ski-like protein), EOCYE7 (Nepn, Protein Nepn), E7EMR6 (TP53, Cellular tumor antigen p53), E7ESS1 (TP53, Cellular tumor antigen p53), E9PAW7 (TGFBR3, Transforming growth factor beta receptor type 3), E9PCT3 (CAV2, Caveolin), E9PCY9 (TP53, Cellular tumor antigen p53), E9PWD8 (Glg1, Golgi apparatus protein 1), E9Q1K0 (Snx25, Sorting nexin-25), E9Q3F7 (Peg10, Retrotransposon-derived protein PEG10), E9QP59 (Lemd3, Inner nuclear membrane protein Mani), F2Z3V6 (Pdpk1, 3-phosphoinositide-dependent protein kinase 1), F2Z3X6 (Pdpk1, 3-phosphoinositide-dependent protein kinase 1), F2Z3X9 (Pdpk1, 3-phosphoinositide-dependent protein kinase 1), F2Z4A5 (Pdpk1, 3-phosphoinositide-dependent protein kinase 1), F5H1T8 (TDGF1, Teratocarcinoma-derived growth factor 1), F6RSH1 (Glg1, Golgi apparatus protein 1), F8VXK3 (CHST11, Carbohydrate sulfotransferase 11), F8WHM5 (Glg1, Golgi apparatus protein 1), G4Y083 (p53, p53), HOY7G9 (HTRA1, Serine protease HTRA1), H2EHT1 (TP53, Cellular tumor antigen p53), H3BL51 (Peg10, Retrotransposon-derived protein PEG10), H3BL85 (Onecut2, One cut domain family member), H3BQT1 (GLG1, Golgi apparatus protein 1), H7C4V3 (SKIL, Ski-like protein), I7HIK9 (Trp53, Cellular tumor antigen p53), K7PPA8 (TP53, Cellular tumor antigen p53), LOEQ05 (TP53, Cellular tumor antigen p53), LOES54 (TP53, Tumor suppressor p53), O08755 (Onecut1, Hepatocyte nuclear factor 6), O14980 (XPO1, Exportin-1), O15105 (SMAD7, Mothers against decapentaplegic homolog 7), O15165 (LDLRAD4, Low-density lipoprotein receptor class A domain-containing protein 4), O15530 (PDPK1, 3-phosphoinositide-dependent protein kinase 1), O35182 (Smad6, Mothers against decapentaplegic homolog 6), O35253 (Smad7, Mothers against decapentaplegic homolog 7), O43294 (TGFB1I1, Transforming growth factor beta-1-induced transcript 1 protein), O43541 (SMAD6, Mothers against decapentaplegic homolog 6), O60543 (CIDEA, Cell death activator CIDE-A), O70302 (Cidea, Cell death activator CIDE-A), O70366 (Trp53, Cellular tumor antigen p53), O75807 (PPP1R15A, Protein phosphatase 1 regulatory subunit 15A), O88393 (Tgfbr3, Transforming growth factor beta receptor type 3), O95405 (ZFYVE9, Zinc finger FYVE domain-containing protein 9), O95948 (ONECUT2, One cut domain family member 2), P01137 (TGFB1, Transforming growth factor beta-1), P02340 (Tp53, Cellular tumor antigen p53), PO4426 (Wnt1, Proto-oncogene Wnt-1), PO4628 (WNT1, Proto-oncogene Wnt-1), PO4637 (TP53, Cellular tumor antigen p53), POCG47 (UBB, Polyubiquitin-B), POCG48 (UBC, Polyubiquitin-C), P10600 (TGFB3, Transforming growth factor beta-3), P11021 (HSPA5, 78 kDa glucose-regulated protein), P12755 (SKI, Ski oncogene), P12757 (SKIL, Ski-like protein), P13385 (TDGF1, Teratocarcinoma-derived growth factor 1), P17125 (Tgfb3, Transforming growth factor beta-3), P17813 (ENG, Endoglin), P20029 (Hspa5, 78 kDa glucose-regulated protein), P30039 (PBLD, Phenazine biosynthesis-like domain-containing protein), P35555 (FBN1, Fibrillin-1), P35556 (FBN2, Fibrillin-2), P35813 (PPM1A, Protein phosphatase 1A), P36873 (PPP1CC, Serine/threonine-protein phosphatase PP1-gamma catalytic subunit), P36897 (TGFBR1, TGF-beta receptor type-1), P37173 (TGFBR2, TGF-beta receptor type-2), P43699 (NKX2-1, Homeobox protein Nkx-2.1), P49443 (Ppm1a, Protein phosphatase 1A), P50220 (Nkx2-1, Homeobox protein Nkx-2.1), P51636 (CAV2, Caveolin-2), P51865 (Tdgf1, Teratocarcinoma-derived growth factor), P62136 (PPP1CA, Serine/threonine-protein phosphatase PP1-alpha catalytic subunit), P62140 (PPP1CB, Serine/threonine-protein phosphatase PP1-beta catalytic subunit), P62979 (RPS27A, Ubiquitin-40S ribosomal protein S27a), P62987 (UBA52, Ubiquitin-60S ribosomal protein L40), P78536 (ADAM17, Disintegrin and metalloproteinase domain-containing protein 17), P83105 (HTRA4, Serine protease HTRA4), P83110 (HTRA3, Serine protease HTRA3), P84022 (SMAD3, Mothers against decapentaplegic homolog 3), P84550 (SKOR1, SKI family transcriptional corepressor 1), Q03112 (MECOM, MDS1 and EVI1 complex locus protein EVI1), Q03167 (TGFBR3, Transforming growth factor beta receptor type 3), QOPKTS (Tumor protein p53 variant), Q13145 (BAMBI, BMP and activin membrane-bound inhibitor homolog), Q13526 (PIN1, Peptidyl-prolyl cis-trans isomerase NIMA-interacting 1), Q14766 (LTBP1, Latent-transforming growth factor beta-binding protein 1), Q15796 (SMAD2, Mothers against decapentaplegic homolog 2), Q1HGV1 (TP53, Mutant p53 tumor suppressor), Q2VWA4 (SKOR2, SKI family transcriptional corepressor 2), Q3TB81 (Ski1, Putative uncharacterized protein), Q3TI47 (Hspa5, Putative uncharacterized protein), Q3TKF8 (Hspa5, Putative uncharacterized protein), Q3TMG0 (Glg1, Putative uncharacterized protein), Q3TQJ9 (Ski1, Putative uncharacterized protein), Q3TRA0 (Ski1, Putative uncharacterized protein), Q3TRQ9 (Tgfb3, Putative uncharacterized protein), Q3TTJ9 (Tgfb3, Putative uncharacterized protein), Q3TUS2 (Hspa5, Putative uncharacterized protein), Q3TWF2 (Hspa5, Putative uncharacterized protein), Q3U6V3 (Hspa5, Putative uncharacterized protein), Q3U7T8 (Hspa5, Putative uncharacterized protein), Q3U835 (Prdm16, Putative uncharacterized protein), Q3U9G2 (Hspa5, Putative uncharacterized protein), Q3UEC0 (Adam17, Putative uncharacterized protein), Q3UEM8 (Hspa5, Putative uncharacterized protein), Q3UEW8 (Pdpk1, Putative uncharacterized protein), Q3UGQ1 (Trp53, Cellular tumor antigen p53), Q3UPN3 (Dand5, Putative uncharacterized protein), Q3UR96 (Wnt1, Protein Wnt), Q3UZP8 (Tdgf1, Putative uncharacterized protein), Q3ZAT5 (Onecut2, Homeobox protein cut-like), Q3ZT31 (Snx25, Sorting nexin-25), Q496P6 (Onecut2, Onecut2 protein), Q53WR6 (Glg1, E-selectin ligand 1), Q53X57 (CAV2, Caveolin), Q549C9 (Trp53, Cellular tumor antigen p53), Q60665 (Ski1, Ski-like protein), Q60698 (Ski, Ski oncogene), Q60979 (Ski1, SnoN protein), Q61543 (Glg1, Golgi apparatus protein 1), Q61554 (Fbn1, Fibrillin-1), Q61555 (Fbn2, Fibrillin-2), Q62219 (Tgfbli1, Transforming growth factor beta-1-induced transcript 1 protein), Q64451 (Trp53, Cellular tumor antigen p53), Q66X47 (Transforming growth factor beta-3), Q67FY2 (Bcl91, B-cell CLL/lymphoma 9-like protein), Q6EMK4 (VASN, Vasorin), Q6IT77 (p53 tumor suppressor), Q6LDJ6 (TGFB3, Transforming growth factor-beta 3), Q6NV61 (Ski, Ski protein), Q6P528 (ASPN, ASPN protein), Q6P8X1 (Snx6, Sorting nexin-6), Q6TDG9 (Trp53, Tumor supressor p53), Q6TV14 (TGFB3, Transforming growth factor beta 3), Q6TV15 (TGFB3, Transforming growth factor beta 3), Q6TV16 (TGFB3, Transforming growth factor beta 3), Q6X7S9 (Eid2, EP300-interacting inhibitor of differentiation 2), Q6XBJ3 (Onecut2, One cut domain family member 2), Q6YHK3 (CD109, CD109 antigen), Q6ZMF1 (cDNA F1123967 fis, clone HEP16652, highly similar to Golgi apparatus protein 1), Q712N7 (caveolin-2, Caveolin), Q761V2 (p53, P53), Q76LW6 (Dand5, DAN domain family member 5), Q7TQ06 (Tdgf1, Tdgf1 protein), Q7TQF4 (Snx25, Snx25 protein), Q7TSK7 (Adamts12, ADAMTS-like protein 2), Q7Z459 (SKI, Ski oncoprotein), Q7Z461 (SKI, Ski oncoprotein), Q7Z462 (SKI, Ski oncoprotein), Q80ZA1 (Trp53, Cellular tumor antigen p53), Q810Z4 (PDK1), Q86TG7 (PEG10, Retrotransposon-derived protein PEG10), Q86TH1 (ADAMTSL2, ADAMTS-like protein 2), Q86UU0 (BCL9L, B-cell CLL/lymphoma 9-like protein), Q8BMW1 (Nepn, Putative uncharacterized protein), Q8BNF5 (Prdm16, Putative uncharacterized protein), Q8BQH1 (Glg1, Putative uncharacterized protein), Q8BSC0 (Smurf1, Putative uncharacterized protein), Q8BWJ4 (Ldlrad4, Low-density lipoprotein receptor class A domain-containing protein 4), Q8BX46 (Skor1, SKI family transcriptional corepressor 1), Q8C526 (Trp53, Cellular tumor antigen p53), Q8KOR3 (Ski, Ski protein), Q8N5H3 (FAM89B, Protein FAM89B), Q8N6I1 (EID2, EP300-interacting inhibitor of differentiation 2), Q8N907 (DAND5, DAN domain family member 5), Q8R422 (Cd109, CD109 antigen), Q91XH8 (Trp53, Cellular tumor antigen p53), Q91YU7 (Tgfb3, Transforming growth factor, beta 3), Q923E4 (Sirt1, NAD-dependent protein deacetylase sirtuin-1), Q924U4 (Cav2, Caveolin), Q92743 (HTRA1, Serine protease HTRA1), Q92896 (GLG1, Golgi apparatus protein 1), Q969W9 (PMEPA1, Protein TMEPAI), Q96EB6 (SIRT1, NAD-dependent protein deacetylase sirtuin-1), Q96PU5 (NEDD4L, E3 ubiquitin-protein ligase NEDD4-like), Q99J68 (Bcl91, Bcl91 protein), Q99KU4 (Ski, Ski protein), Q99MQ4 (Aspn, Asporin), Q9BXN1 (ASPN, Asporin), Q9CQ76 (Nepn, Nephrocan), Q9CS56 (Prdm16, Putative uncharacterized protein), Q9CTE9 (Ski, Putative uncharacterized protein), Q9CTL6 (Aspn, Putative uncharacterized protein), Q9CUN6 (Smurf1, E3 ubiquitin-protein ligase SMURF1), Q9CXN7 (Pbld2, Phenazine biosynthesis-like domain-containing protein 2), Q9CZT5 (Vasn, Vasorin), Q9D0L6 (Bambi, BMP and activin membrane-bound inhibitor homolog), Q9D236 (Htra3, Serine protease HTRA3), Q9D7R2 (Pmepal, Protein TMEPAI), Q9DC41 (Hspa5, Putative uncharacterized protein), Q9ER40 (Trp53, Cellular tumor antigen p53), Q9H3E2 (SNX25, Sorting nexin-25), Q9HAU4 (SMURF2, E3 ubiquitin-protein ligase SMURF2), Q9HAZ2 (PRDM16, PR domain zinc finger protein 16), Q9HCE7 (SMURF1, E3 ubiquitin-protein ligase SMURF1), Q9JME2 (Chst11, Carbohydrate sulfotransferase 11), Q9NPF2 (CHST11, Carbohydrate sulfotransferase 11), Q9NYA4 (MTMR4, Myotubularin-related protein 4), Q9QUI1 (Fam89b, Protein FAM89B), Q9R118 (Htra1, Serine protease HTRA1), Q9UBC0 (ONECUT1, Hepatocyte nuclear factor 6), Q9UNE7 (STUB1, E3 ubiquitin-protein ligase CHIP), Q9UNH7 (SNX6, Sorting nexin-6), Q9WVC3 (Cav2, Caveolin-2), Q9Y2U8 (LEMD3, Inner nuclear membrane protein Mani), Q9Y3F4 (STRAP, Serine-threonine kinase receptor-associated protein), Q9Y4E8 (USP15, Ubiquitin carboxyl-terminal hydrolase 15), Q9Y5K5 (UCHL5, Ubiquitin carboxyl-terminal hydrolase isozyme L5), Q9ZOF8 (Adam17, Disintegrin and metalloproteinase domain-containing protein 17), Q9Z1Z2 (Strap, Serine-threonine kinase receptor-associated protein), Q9Z2A0 (Pdpk1, 3-phosphoinositide-dependent protein kinase 1), S5LQU8 (TP53, Cellular tumor antigen p53), V9HWB4 (HEL-S-89n, Epididymis secretory sperm binding protein Li 89n), and the like.

In some instances, negative regulators of BMP signaling include proteins that are FK506 binding proteins. Such FK506 binding proteins include but are not limited to, e.g., those proteins identified by the gene ontology term GO:0005528 as interacting selectively and non-covalently with the 23-membered macrolide lactone FK506, which includes UniProtKB IDs: A2A4H9 (Fkbp10, Peptidyl-prolyl cis-trans isomerase FKBP10), A9E3L2 (Fkbp1b, Peptidyl-prolyl cis-trans isomerase), B8JJC2 (Fkbp5, Peptidyl-prolyl cis-trans isomerase), C9KOZ7 (Fkbp8, FK-506-binding protein 38), D3YWB6 (Fkbp14, Peptidyl-prolyl cis-trans isomerase FKBP14), D3Z597 (Fkbp8, Peptidyl-prolyl cis-trans isomerase FKBP8), D6RDE2 (Fkbp4, Peptidyl-prolyl cis-trans isomerase), D6RDT0 (Fkbp14, Peptidyl-prolyl cis-trans isomerase), F6S2D5 (Fkbp4, Peptidyl-prolyl cis-trans isomerase), F6W360 (Fkbp10, Peptidyl-prolyl cis-trans isomerase), F6WP10 (Fkbp8, Peptidyl-prolyl cis-trans isomerase FKBP8), F6X9I3 (Fkbp1a, Peptidyl-prolyl cis-trans isomerase), F7CAT1 (Fkbp4, Peptidyl-prolyl cis-trans isomerase), F8W6G9 (FKBP1B, Peptidyl-prolyl cis-trans isomerase), G3UY63 (Fkbp1, FK506-binding protein-like), H3BJI5 (Fkbp7, Peptidyl-prolyl cis-trans isomerase), O35450 (Fkbp1, FK506-binding protein-like), O35465 (Fkbp8, Peptidyl-prolyl cis-trans isomerase FKBP8), O54998 (Fkbp7, Peptidyl-prolyl cis-trans isomerase FKBP7), O75344 (FKBP6, Inactive peptidyl-prolyl cis-trans isomerase FKBP6), O95302 (FKBP9, Peptidyl-prolyl cis-trans isomerase FKBP9), O95644 (NFATC1, Nuclear factor of activated T-cells, cytoplasmic 1), P26883 (Fkbp1a, Peptidyl-prolyl cis-trans isomerase FKBP1A), P26885 (FKBP2, Peptidyl-prolyl cis-trans isomerase FKBP2), P30416 (Fkbp4, Peptidyl-prolyl cis-trans isomerase FKBP4), P45878 (Fkbp2, Peptidyl-prolyl cis-trans isomerase FKBP2), P59024 (Fkbp14, Peptidyl-prolyl cis-trans isomerase FKBP14), P62942 (FKBP1A, Peptidyl-prolyl cis-trans isomerase FKBP1A, a.k.a. FKBP12), P68106 (FKBP1B, Peptidyl-prolyl cis-trans isomerase FKBP1B), Q00688 (FKBP3, Peptidyl-prolyl cis-trans isomerase FKBP3), Q02790 (FKBP4, Peptidyl-prolyl cis-trans isomerase FKBP4), Q05BQ9 (Fkbp14, Fkbp14 protein), Q13451 (FKBP5, Peptidyl-prolyl cis-trans isomerase FKBP5), Q14318 (FKBP8, Peptidyl-prolyl cis-trans isomerase FKBP8), Q1JUQ6 (Fkbp1a, FK506 binding protein12), Q1JUQ7 (Fkbp1a, FK506 binding protein12-T2), Q1JUQ8 (Fkbp1a, FK506 Binding Protein12-T1), Q3TND1 (Fkbp2, Peptidyl-prolyl cis-trans isomerase), Q3TQQ3

(Fkbp14, Putative uncharacterized protein), Q3TX72 (Fkbp5, Putative uncharacterized protein), Q3UB60 (Ppid, Putative uncharacterized protein), Q3UBAO (Fkbp1a, Peptidyl-prolyl cis-trans isomerase), Q3UBU9 (Fkbp3, Peptidyl-prolyl cis-trans isomerase), Q3UKJ3 (Fkbp1a, Peptidyl-prolyl cis-trans isomerase), Q3ULN5 (Fkbp1a, Peptidyl-prolyl cis-trans isomerase), Q3UND3 (Fkbp2, Peptidyl-prolyl cis-trans isomerase), Q3UNJ3 (Fkbp10, Putative uncharacterized protein), Q3UU11 (Fkbp7, FK506 binding protein 7), Q3V038 (Ttc9, Tetratricopeptide repeat protein 9A), Q4FJN2 (Fkbp5, FK506 binding protein 5), Q542Q0 (Fkbp14, FK506 binding protein 14, isoform CRA_a), Q5VVH2 (FKBP1C, Peptidyl-prolyl cis-trans isomerase), Q61576 (Fkbp10, Peptidyl-prolyl cis-trans isomerase FKBP10), Q62446 (Fkbp3, Peptidyl-prolyl cis-trans isomerase FKBP3), Q64378 (Fkbp5, Peptidyl-prolyl cis-trans isomerase FKBP5), Q6P3Y6 (Ttc9c, Tetratricopeptide repeat protein 9C), Q80YE1 (Fkbp1b, Peptidyl-prolyl cis-trans isomerase), Q810A3 (Ttc9c, Tetratricopeptide repeat protein 9C), Q810R7 (Fkbp1b, Peptidyl-prolyl cis-trans isomerase), Q8BMX6 (Ppid, Putative uncharacterized protein), Q8CBS1 (Fkbp4, Putative uncharacterized protein), Q8CF43 (Fkbp6, Putative uncharacterized protein), Q8N6N2 (TTC9B, Tetratricopeptide repeat protein 9B), Q91XW8 (Fkbp6, Inactive peptidyl-prolyl cis-trans isomerase FKBP6), Q96AY3 (FKBP10, Peptidyl-prolyl cis-trans isomerase FKBP10), Q9CR16 (Ppid, Peptidyl-prolyl cis-trans isomerase D), Q9D1M7 (Fkbp11, Peptidyl-prolyl cis-trans isomerase FKBP11), Q9D6E4 (Ttc9b, Tetratricopeptide repeat protein 9B), Q9NWM8 (FKBP14, Peptidyl-prolyl cis-trans isomerase FKBP14), Q9NYL4 (FKBP11, Peptidyl-prolyl cis-trans isomerase FKBP11), Q9UIM3 (FKBPL, FK506-binding protein-like), Q9Y680 (FKBP7, Peptidyl-prolyl cis-trans isomerase FKBP7), Q9Z247 (Fkbp9, Peptidyl-prolyl cis-trans isomerase FKBP9), Q9Z2I2 (Fkbp1b, Peptidyl-prolyl cis-trans isomerase FKBP1B), and the like.

In some instances, a BMP repressor may be any molecule that inhibits the expression of one or more BMP target genes. The expression of such BMP target genes, in some cases serve as useful markers for the activation of BMP signaling, e.g., following administration of an agent that activates BMP signaling, and, in some cases, may be useful in measuring the degree to which BMP signaling is activated and/or to determine the effective amount of an agent that activates BMP to be administered to a subject. BMP target genes include but are not limited to e.g., ID4 (RefSeq IDs: NP_001537.1 and NM_001546.3, UniProtKB ID: P47928), CDKN1B (RefSeq IDs: NP_004055.1 and NM_004064.4, UniProtKB ID: Q6I9V6), as described in e.g., Samanta & Kessler (2004), Miyazono & Miyazawa (2002, Mysorekar et al. (2009), Franzen & Heldin (2001), Chang et al. (2009), the disclosures of which are incorporated herein by reference. In some instances, BMP activation may be determined and/or measured by evaluating the expression of one or more SMAD target genes, including but not limited to, e.g., BMP responsive genes (e.g., BGLAP (osteocalcin), DLX2, ID1, ID2, ID3, ID4, JUNB, SOX4, STAT1, etc., and those described in, e.g., Shin et al. (2014) *Cancer Cell.* 26:521-533, the disclosure of which is incorporated herein by reference in its entirety), TGF-β responsive genes (e.g., CDC25A, CDKN1A (p21WAF1/p21CIP1), CDKN2B (p15LNK2B), COL1A1, COL1A2, COL3A1, FOS, GSC (goosecoid), IGF1, IGFBP3, IL6, ITGB5 (integrin B5), ITGB7 (integrin B7), JUN, JUNB, MYC, PDGFB, SERPINE 1 (PAI-1), TSC22D1 (TGFB1I4), TGFBI, TGIF1), and the like.

In one embodiment, the agent that activates BMP signaling is FK506 or an analog thereof. FK506 (PubChem CID 445643; also known as Fujimycin, Prograf, Protopic, Tacrolimus anhydrous, Tsukubaenolide, Advagraf) is a 23-member ring macrolide lactone having the following chemical structure:

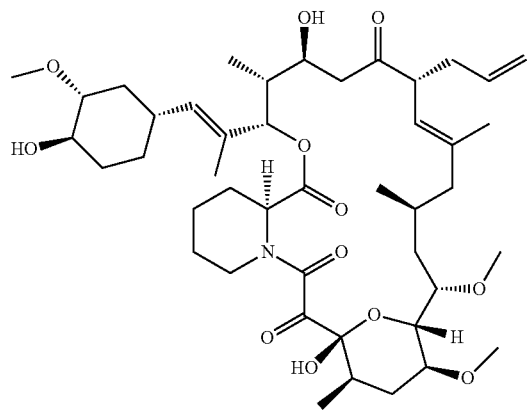 [SMILES: C=CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]

Analogs and derivatives of FK506 and related compounds include but are not limited to, e.g., AP1903, L-685,818, L-732,531, Ascomycin (L-683,590), L-688,617, A-119435, derivatives of ascomycin (e.g., (R)-[18-OH]ascomycin, (S)-[18-OH]ascomycin, etc.), those described in Gopalakrishnan et al. (2012) *J Med Chem.* 55(9):4114-22; Petros et al. (1992) *FEBS Letters.* 308(3):309-14; Klettner & Herdgen (2003) *Curr Drug Targets CNS Neurol Disord.* 2(3):153-62; Moss et al. (2012) *Med Chem Comm.* 4:324-331; and Dumont F J (2000) *Curr Med Chem.* 7:731-748, those described in U.S. Pat. Pub. App. Nos.: 20130230559, 20040077676, and 20060160838, those described in U.S. Pat. Nos. 4,894,366, 4,929,611, 4,956,352, 5,254,562, 5,250,678, 532,248, 5,693,648, 5,262,533, 5,284,840, 5,208, 241, 5,208,228, 5,208,228, 5,162,334, and 5,143,918, the disclosures of which are incorporated herein by reference.

Methods and Compositions

Aspects of the disclosure include methods and compositions for inducing BMP signaling in an individual, e.g., through the administration of an agent that activates BMP signaling. Because such methods can be used to treat an individual, such methods can also be referred to as methods of treating an individual.

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. For example, a preventative treatment, i.e. a prophylactic treatment, may include a treatment that effectively prevents new tumor initiation or a treatment that effectively prevents or controls tumor progression or tumor spread. In some instances, the treatment may result in a treatment response, such as a complete response or a partial response. The term "treatment" encompasses any treatment of a disease in a mammal, particularly a human, and includes: (a) preventing the disease and/or symptom(s) from occurring in a subject who may be predisposed to the disease or symptom(s) but has not yet been diagnosed as having it; (b) inhibiting the disease and/or symptom(s), i.e., arresting development of a disease and/or the associated symptoms; or (c) relieving the disease and the associated symptom(s), i.e., causing regression of the disease and/or symptom(s). Those in need of treatment can include those already afflicted (e.g., those with cancer, e.g. those having tumors) as well as those in which prevention is desired (e.g., those with increased susceptibility to cancer; those suspected of having cancer, those with an increased risk of developing cancer; those with increased exposure to cancer causing environmental conditions and/or agents, those suspected of having pre-cancerous lesions; those with a pre-cancerous lesion, those having results from cancer screening indicating an increased risk of developing cancer, those having tested positive on an indirect cancer bioassay, those having tested positive for one or more cancer biomarkers, etc.).

A therapeutic treatment is one in which the subject is afflicted prior to administration and a prophylactic treatment is one in which the subject is not afflicted prior to administration. In some embodiments, the subject has an increased likelihood of becoming afflicted or is suspected of having an increased likelihood of becoming afflicted (e.g., relative to a standard, e.g., relative to the average individual, e.g., a subject may have a genetic predisposition to cancer and/or a family history indicating increased risk of cancer), in which case the treatment can be a prophylactic treatment.

In some embodiments, the individual to be treated is an individual with cancer. As used herein "cancer" includes any form of cancer, including but not limited to, e.g.: Acute Lymphoblastic Leukemia (ALL), Acute Myeloid Leukemia (AML), Adrenocortical Carcinoma, AIDS-Related Cancers (e.g., Kaposi Sarcoma, Lymphoma, etc.), Anal Cancer, Appendix Cancer, Astrocytomas, Atypical Teratoid/Rhabdoid Tumor, Basal Cell Carcinoma, Bile Duct Cancer (Extrahepatic), Bladder Cancer, Bone Cancer (e.g., Ewing Sarcoma, Osteosarcoma and Malignant Fibrous Histiocytoma, etc.), Brain Stem Glioma, Brain Tumors (e.g., Astrocytomas, Central Nervous System Embryonal Tumors, Central Nervous System Germ Cell Tumors, Craniopharyngioma, Ependymoma, etc.), Breast Cancer (e.g., female breast cancer, male breast cancer, childhood breast cancer, etc.), Bronchial Tumors, Burkitt Lymphoma, Carcinoid Tumor (e.g., Childhood, Gastrointestinal, etc.), Carcinoma of Unknown Primary, Cardiac (Heart) Tumors, Central Nervous System (e.g., Atypical Teratoid/Rhabdoid Tumor, Embryonal Tumors, Germ Cell Tumor, Lymphoma, etc.), Cervical Cancer, Childhood Cancers, Chordoma, Chronic Lymphocytic Leukemia (CLL), Chronic Myelogenous Leukemia (CML), Chronic Myeloproliferative Neoplasms, Colon Cancer, Colorectal Cancer, Craniopharyngioma, Cutaneous T-Cell Lymphoma, Duct (e.g., Bile Duct, Extrahepatic, etc.), Ductal Carcinoma In Situ (DCIS), Embryonal Tumors, Endometrial Cancer, Ependymoma, Esophageal Cancer, Esthesioneuroblastoma, Ewing Sarcoma, Extracranial Germ Cell Tumor, Extragonadal Germ Cell Tumor, Extrahepatic Bile Duct Cancer, Eye Cancer (e.g., Intraocular Melanoma, Retinoblastoma, etc.), Fibrous Histiocytoma of Bone (e.g., Malignant, Osteosarcoma, ect.), Gallbladder Cancer, Gastric (Stomach) Cancer, Gastrointestinal Carcinoid Tumor, Gastrointestinal Stromal Tumors (GIST), Germ Cell Tumor (e.g., Extracranial, Extragonadal, Ovarian, Testicular, etc.), Gestational Trophoblastic Disease, Glioma, Hairy Cell Leukemia, Head and Neck Cancer, Heart Cancer, Hepatocellular (Liver) Cancer, Histiocytosis (e.g., Langerhans Cell, etc.), Hodgkin Lymphoma, Hypopharyngeal Cancer, Intraocular Melanoma, Islet Cell Tumors (e.g., Pancreatic Neuroendocrine Tumors, etc.), Kaposi Sarcoma, Kidney Cancer (e.g., Renal Cell, Wilms Tumor, Childhood Kidney Tumors, etc.), Langerhans Cell Histiocytosis, Laryngeal Cancer, Leukemia (e.g., Acute Lymphoblastic (ALL), Acute Myeloid (AML), Chronic Lymphocytic (CLL), Chronic Myelogenous (CML), Hairy Cell, etc.), Lip and Oral Cavity Cancer, Liver Cancer (Primary), Lobular Carcinoma In Situ (LCIS), Lung Cancer (e.g., Non-Small Cell, Small Cell, etc.), Lymphoma (e.g., AIDS-Related, Burkitt, Cutaneous T-Cell, Hodgkin, Non-Hodgkin, Primary Central Nervous System (CNS), etc.), Macroglobulinemia (e.g., Waldenström, etc.), Male Breast Cancer, Malignant Fibrous Histiocytoma of Bone and Osteosarcoma, Melanoma, Merkel Cell Carcinoma, Mesothelioma, Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia (e.g., Chronic (CML), etc.), Myeloid Leukemia (e.g., Acute (AML), etc.), Myeloproliferative Neoplasms (e.g., Chronic, etc.), Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer (e.g., Lip, etc.), Oropharyngeal Cancer, Osteosarcoma and Malignant Fibrous Histiocytoma of Bone, Ovarian Cancer (e.g., Epithelial, Germ Cell Tumor, Low Malignant Potential Tumor, etc.), Pancreatic Cancer, Pancreatic Neuroendocrine Tumors (Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Pleuropulmonary Blastoma, Primary Central Nervous System (CNS) Lymphoma, Prostate Cancer, Rectal Cancer, Renal Cell (Kidney) Cancer, Renal Pelvis and Ureter, Transitional Cell Cancer, Retinoblastoma, Rhabdomyo sarcoma, Salivary Gland Cancer, Sarcoma (e.g., Ewing, Kaposi, Osteosarcoma, Rhabdomyosarcoma, Soft Tissue, Uterine, etc.), Sézary Syndrome, Skin Cancer (e.g., Childhood, Melanoma, Merkel Cell Carcinoma, Nonmelanoma, etc.), Small Cell Lung Cancer, Small Intestine Cancer, Soft Tissue Sarcoma, Squamous Cell Carcinoma, Squamous Neck Cancer (e.g., with Occult Primary, Metastatic, etc.), Stomach (Gastric) Cancer, T-Cell Lymphoma, Testicular Cancer, Throat Cancer, Thymoma and Thymic Carcinoma, Thyroid Cancer, Transitional Cell Cancer of the Renal Pelvis and Ureter, Ureter and Renal Pelvis Cancer, Urethral Cancer, Uterine Cancer (e.g., Endometrial, etc.), Uterine Sarcoma, Vaginal Cancer, Vulvar Cancer, Waldenström Macroglobulinemia, Wilms Tumor, and the like. In some instances the cancer to be treated is an epithelial cancer (i.e., a carcinoma) or a cancer derived from an epithelial cell type, including but not limited to, e.g.: acinar carcinoma, acinic cell carcinoma, acinous carcinoma, adenocystic carcinoma, adenoid cystic carcinoma, adenosquamous carcinoma, adnexal carcinoma, adrenocortical carcinoma, alveolar carcinoma, ameloblastic carcinoma, apocrine carcinoma, basal cell carcinoma, bronchiolo alveolar carcinoma, bronchogenic carcinoma, cholangiocellular carcinoma, chorionic carcinoma, clear cell carcinoma, colloid carcinoma, cribriform carcinoma, ductal carcinoma in situ, embryonal carcinoma, carcinoma en cuirasse, endometrioid carcinoma, epidermoid carcinoma, carcinoma ex mixed tumor, carcinoma ex pleomorphic adenoma, follicular carcinoma of thyroid gland, hepatocellular carcinoma, carcinoma in situ, intraductal carcinoma, Hürthle cell carcinoma, inflammatory carcinoma of the breast, large cell carcinoma, invasive lobular carcinoma, lobular carcinoma, lobular carcinoma in situ (LCIS), medullary carcinoma, meningeal carcinoma, Merkel cell carcinoma, mucinous carcinoma, mucoepidermoid carcinoma, nasopharyngeal carcinoma, non-small cell carcinoma, non-small cell lung carcinoma (NSCLC), oat cell carcinoma, papillary carcinoma, renal cell carcinoma, scirrhous carcinoma, sebaceous carcinoma, carcinoma simplex, signet-ring cell carcinoma, small cell carcinoma, small cell lung carcinoma, spindle cell carcinoma, squamous cell carcinoma, terminal duct carcinoma, transitional cell carcinoma, tubular carcinoma, verrucous carcinoma, and the like. In some cases, the individual has recently undergone treatment for cancer (e.g., chemotherapy, radiation therapy, etc.) and are therefore at risk for recurrence. Any and all cancers are suitable cancers to be treated by the subject methods, compositions, and kits.

Methods of Administration

In general terms, the activator of BMP signaling, e.g., FK506, may be administered to the subject in the instant method in a similar way to how FK506 is administered in immunosuppressive applications. For example, the activator of BMP signaling, e.g., FK506, may be present in a pharmaceutically acceptable excipient, and it may be administered intravenously. Alternatively, it may be administered orally or topically.

In some embodiments, the activator of BMP signaling is administered at a lower dose, and thus its usual side effects may be decreased. Typical side effects of FK506, e.g., include infection, cardiac damage, hypertension, blurred vision, liver and kidney problems (tacrolimus nephrotoxicity), hyperkalemia, hypomagnesemia, hyperglycemia, diabetes mellitus, itching, lung damage (sirolimus also causes lung damage), and various neuropsychiatric problems such as loss of appetite, insomnia, posterior reversible encephalopathy syndrome, confusion, weakness, depression, cramps, neuropathy, seizures, tremors, and catatonia.

In some embodiments, FK506 is administered in a "low" dose or a "subimmunosuppressive" dose. By low dose FK506 or subimmunosuppressive FK506 is meant that FK506 is administered at a dose and regimen that provides an FK506 serum concentration that is much lower than the FK506 serum concentration commonly used in immunosuppressive applications (which is typically 5-15 ng/ml). For example, in certain embodiments of the instant method, the FK506 is administered at a dose and regimen that provides an FK506 serum concentration of as 0.05 ng/ml to 1 ng/ml, e.g., 0.1 ng/ml to 0.5 ng/ml, 0.15 ng/ml to 0.3 ng/ml or e.g. 0.1-0.2 ng/ml. In part because FK-506 is metabolized by the cytochrome P450 system, the exact dosing may vary between patients. The FK506 may be administered once a day or more, e.g., twice per day. In immunosuppressive applications, FK506 is normally given twice daily with the goal to reach FK-506 serum levels of 5-15 ng/ml. The treatment is started at 0.5 mg twice daily and then up-titrated according to the measured FK506 serum level. In some cases a dosing of 0.075 mg/kg/day is recommended to reach a serum level of 5-10 ng/ml. In some embodiments of the instant method, the goal is to reach a serum level of about 0.2 ng/ml, which is about 1/20 of the immunosuppressive serum level. In this case, an initial dose of 0.001 mg/kg day to 0.01 mg/kg day (e.g., 0.002 mg kg/day to 0.05 mg/kg/day may be sufficient, and the does can be up-titrated according to the measured FK506 serum level. The subject may be any mammal, e.g., a human, rat, or mouse, for example. In particular cases, the FK506 may reach a serum concentration as low as 0.1-0.2 ng/ml (e.g., 0.10 to 0.12, 0.12 to 0.14, 0.14 to 0.16, 0.16 to 0.18 or 0.18 to 0.20, however serum a concentration in the range of 0.2 to 2 ng/ml, e.g., 0.2, 0.5, 1 and 2 ng/ml may be acceptable. In particular cases, the FK506 may reach a serum concentration of <1.0, 1.5-2.5, or 3-5 ng/ml.

In some instances, the dosage of an agent that activates BMP, e.g., FK506, to be used in a human subject may be based on an effective dose of the agent as determined through pre-clinical testing, e.g., animal trials. For example, in some instances, a dosage, e.g., a low dosage of FK506, found to be an effective dose in animal studies, e.g., mouse studies, may be converted to a human equivalent dose for use in humans. In one embodiment, based on studies in mice demonstrating effectiveness of low dosages of FK506 ranging from 0.01 to 0.1 mg/kg/day, a human subject in need of treatment is correspondingly administered FK506 at a dose ranging from 0.8 to 8 µg/kg/day, including e.g., 0.8 µg/kg/day, 0.9 µg/kg/day, 1 µg/kg/day, 1.1 µg/kg/day, 1.2 µg/kg/day, 1.3 µg/kg/day, 1.4 µg/kg/day, 1.5 µg/kg/day, 1.6 µg/kg/day, 1.7 µg/kg/day, 1.8 µg/kg/day, 1.9 µg/kg/day, 2 µg/kg/day, 2.1 µg/kg/day, 2.2 µg/kg/day, 2.3 µg/kg/day, 2.4 µg/kg/day, 2.5 µg/kg/day, 2.6 µg/kg/day, 2.7 µg/kg/day, 2.8 µg/kg/day, 2.9 µg/kg/day, 3 µg/kg/day, 3.1 µg/kg/day, 3.2 µg/kg/day, 3.3 µg/kg/day, 3.4 µg/kg/day, 3.5 µg/kg/day, 3.6 µg/kg/day, 3.7 µg/kg/day, 3.8 µg/kg/day, 3.9 µg/kg/day, 4 µg/kg/day, 4.1 µg/kg/day, 4.2 µg/kg/day, 4.3 µg/kg/day, 4.4 µg/kg/day, 4.5 µg/kg/day, 4.6 µg/kg/day, 4.7 µg/kg/day, 4.8 µg/kg/day, 4.9 µg/kg/day, 5 µg/kg/day, 5.1 µg/kg/day, 5.2 µg/kg/day, 5.3 µg/kg/day, 5.4 µg/kg/day, 5.5 µg/kg/day, 5.6 µg/kg/day, 5.7 µg/kg/day, 5.8 µg/kg/day, 5.9 µg/kg/day, 6 µg/kg/day, 6.1 µg/kg/day, 6.2 µg/kg/day, 6.3 µg/kg/day, 6.4 µg/kg/day, 6.5 µg/kg/day, 6.6 µg/kg/day, 6.7 µg/kg/day, 6.8 µg/kg/day, 6.9 µg/kg/day, 7 µg/kg/day, 7.1 µg/kg/day, 7.2 µg/kg/day, 7.3 µg/kg/day, 7.4 µg/kg/day, 7.5 µg/kg/day, 7.6 µg/kg/day, 7.7 µg/kg/day, 7.8 µg/kg/day, 7.9 µg/kg/day, and 8 µg/kg/day. Conversion of an animal dose to human equivalent doses (HED) may, in some instances, be performed using the conversion table and/or algorithm provided by the U.S. Department of Health and Human Services, Food and Drug Administration, Center for Drug Evaluation and Research (CDER) in, e.g., *Guidance for Industry: Estimating the Maximum Safe Starting Dose in Initial Clinical Trials for Therapeutics in Adult Healthy Volunteers* (2005) Food and Drug Administration, 5600 Fishers Lane, Rockville, Md. 20857; (available at www(dot)fda(dot)gov/cder/guidance/index(dot)htm, the disclosure of which is incorporated herein by reference).

TABLE 3

Conversion of Animal Doses to Human Equivalent Doses Based on Body Surface Area

| | To Convert | To Convert Animal Dose in mg/kg to HED[a] in mg/kg, Either: | |
|---|---|---|---|
| | Animal Dose in mg/kg to Dose in mg/m², Multiply by $k_m$ | Divide Animal Dose By | Multiply Animal Dose By |
| Species | | | |
| Human | 37 | — | — |
| Child (20 kg)[b] | 25 | — | — |
| Mouse | 3 | 12.3 | 0.08 |
| Hamster | 5 | 7.4 | 0.13 |
| Rat | 6 | 6.2 | 0.16 |
| Ferret | 7 | 5.3 | 0.19 |
| Guinea pig | 8 | 4.6 | 0.22 |
| Rabbit | 12 | 3.1 | 0.32 |
| Dog | 20 | 1.8 | 0.54 |

TABLE 3-continued

Conversion of Animal Doses to Human
Equivalent Doses Based on Body Surface Area

| | To Convert<br>Animal Dose<br>in mg/kg to Dose in<br>mg/m$^2$, Multiply by k$_m$ | To Convert Animal<br>Dose in mg/kg to<br>HED$^a$ in mg/kg, Either: | |
|---|---|---|---|
| | | Divide<br>Animal<br>Dose By | Multiply<br>Animal Dose By |
| Primates: | | | |
| Monkeys$^c$ | 12 | 3.1 | 0.32 |
| Marmoset | 6 | 6.2 | 0.16 |
| Squirrel monkey | 7 | 5.3 | 0.19 |
| Baboon | 20 | 1.8 | 0.54 |
| Micro-pig | 27 | 1.4 | 0.73 |
| Mini-pig | 35 | 1.1 | 0.95 |

$^a$Assumes 60 kg human. For species not listed or for weights outside the standard ranges, HED can be calculated from the following formula: HED = animal dose in mg/kg × (animal weight in kg/human weight in kg) 0.33.
$^b$This km value is provided for reference only since healthy children will rarely be volunteers for phase 1 trials.
$^c$For example, cynomolgus, rhesus, and stumptail.

In some instances, an effective dose of an agent that activates BMP signaling described herein may be co-administered with one or more additional agents. For example, an effective dose of an agent that activates BMP signaling according to the methods described herein may be co-administered with one or more additional agents. Additional agents useful in such co-administration include agents that improve the overall effectiveness of the effective dose of an agent that activates BMP signaling or decrease the dose of an agent that activates BMP signaling necessary to achieve an effect essentially equal to administration of an effective dose of the agent that activates BMP signaling without the additional agent. Non-limiting examples of additional agents that may be co-administered with an agent that activates BMP signaling according to the methods described herein include: agents that activate BMP signaling (e.g., small molecule agents (e.g., isoliquiritigenin, 4'-hydroxychalcone, apigenin, diosmetin, etc.), peptide and polypeptide agents (e.g., BMP peptides and fragments thereof, etc.), nucleic acid agents (e.g., interfering nucleic acids targeting repressors of BMP signaling, and the like), etc.), agents that modulate TNF-β signaling upstream of BMP signaling (e.g., agents that activate BMP pathway SMADs through the activation of components of the TNF-β signaling pathway, etc.).

In some instances, an additional agent, e.g., useful for co-administration with an effective amount of an agent that activates BMP signaling as described herein, may be an agent that modulates hedgehog (Hh) signaling. In some instances, an agent that modulates Hh signaling may be an agent that inhibits Hh signaling. Hh expression, in particular sonic hedgehog (Shh) expression in humans, is associated with carcinogenesis of certain cancers. Hh associated cancers include but are not limited to, e.g., Gorlin Syndrome cancers, basal cell carcinoma (BCC), skin cancer, pancreatic cancer, gastrointestinal cancer, colon cancer, gastric cancer, bladder cancer, breast cancer, liver cancer, brain cancer, prostate cancer, lung cancer, and those described in, e.g., Onishi H, et al. (2014) World J Gastroenterol. 20(9):2335-42, Abidi A, et al. (2014) Indian J Pharmacol. 46(1):3-12, Bertrand F E, et al. (2012) Cell Cycle. 11(23):4344-51, Saqui-Salces M, et al. (2010) Biochim Biophys Acta. 1803 (7):786-95, Kasper M, et al. (2009) Carcinogenesis. 30(6): 903-11, Omenetti A, et al. (2008) Am J Physiol Gastrointest Liver Physiol. 294(3):G595-8, Katoh Y, et al. (2005) Cancer Biol Ther. 4(10):1050-4, Romer J, et al. (2005) Cancer Res. 65(12):4975-8, Sanchez P, et al. (2005) Cancer Res. 65(8): 2990-2, Watkins D N, et al. (2003) Cell Cycle. 2(3):196-8, the disclosures of which are incorporated herein by reference.

In some instances, an agent that modulates Hh signaling may be an agent that activates Hh signaling. A lack of Hh expression, reduced Hh expression or loss of Hh expression, in particular sonic hedgehog (Shh) expression in humans, is associated with the progression of certain cancers, including but not limited to, e.g., pancreatic cancer and bladder cancer, as described herein and in Lee et al. (2014) PNAS. 111(30): E3091-100, the disclosure of which is incorporated herein by reference in its entirety.

By the term "Hh associated cancers" is meant cancers that at some point in the cancer carcinogenesis and/or cancer progression a Hh gene or protein or a Hh pathway gene or protein is expressed or misexpressed, e.g., over expressed or under expressed, and Hh signaling is elevated or repressed as compared to related non-cancerous cells and/or non-invasive cancerous cells. In some instances, a Hh associated cancer is a cancer in which a Hh or a Hh pathway member is expressed during carcinogenesis, e.g., Hh signaling is active in the cancer forming cell type or the pre-cancerous cell. In some instances, a Hh associated cancer is a cancer in which Hh signaling is elevated, e.g., due to over expression of Hh, due to a mutation in a component of the Hh signaling pathway, due to a constitutively active Hh pathway receptor (e.g., a patched receptor, e.g., PTCH1), etc. In some instances, a Hh associated cancer is a cancer in which Hh signaling is repressed, e.g., through the under expression of a Hh, through a mutation in a component of the Hh signaling pathway, etc. Hh signaling is associated with the maintenance of stem cells, tissue repair, and tissue homeostasis, and in particular, maintenance of epithelial stem cells, epithelial tissue repair, and epithelial tissue homeostasis (see, e.g., Beachy et al. (2004) Nature. 432(7015):324-31 and Jiang & Hui, (2008) Dev Cell. 15(6):801-812) and, as such, in some instances Hh associated cancers that may be treated according to the methods described herein may be epithelial cancers, carcinomas, and cancers derived from epithelial cells or cells of an epithelial lineage.

In some instances, a Hh associated cancer is characterized by dynamic Hh signaling or dynamic changes in Hh signaling and/or expression of Hh pathway components. In some instances, a Hh associated cancer may be associated with elevated Hh signaling during one stage of cancer carcinogenesis and/or progression and may be associated with repressed Hh signaling during another stage of cancer carcinogenesis and/or progression. For example, a Hh associated cancer may be associated with elevated Hh signaling during carcinogenesis and associated with repressed Hh signaling during cancer progression, e.g., during tumor invasion, during tumor growth, during tumor metastasis, etc.

Modulation of the Hh pathway, as described herein, is not limited for use in Hh-associated cancers and may find use in treating cancers in which the cells of the cancer do not significantly express Hh during carcinogenesis or cancer progression or in a particular subpopulation of cancerous cells which essentially do not express Hh during carcinogenesis or cancer progression. As such, Hh modulation, e.g., activation of Hh signaling, may find use in treating cancers by activating or promoting Hh signaling in cancerous cells or cells associated with cancerous cells in which Hh signaling is essentially not active or is not conventionally associated with such cells.

In some instances, modulation of the Hh pathway to treat a subject for cancer as described herein may be performed to modulate Hh signaling in a subpopulation of cells, e.g., a subpopulation of cells most likely to result in a therapeutic effect from the modulation. For example, in some instances, a subject may be administered a Hh modulator, e.g., a Hh agonist, to modulate, e.g., promote or activate, Hh signaling in stromal derived cells. In some instances, e.g., a subject may be administered a Hh modulator, e.g., a Hh antagonist, to modulate, e.g., inhibit or repress, Hh signaling in epithelial derived cells.

In some instances, a subject in need of BMP activation for the treatment of a Hh associated cancer may be treated with an agent that activates BMP and may also be treated by inhibition of Hh signaling, e.g., through inhibition of Hh, e.g., by inhibiting Hh expression Inhibition of Hh and/or inhibition of Hh signaling in a subject may be achieved by any convenient method including but not limited to disruption of Hh expression (e.g., by altering the genomic Hh locus, through the use of interfering nucleic acids targeting Hh and/or Hh pathway components, etc.), disruption of Hh or Hh pathway component function (e.g., through the use of small molecule Hh antagonists and/or Hh pathway antagonists, through the use of peptide or polypeptide Hh antagonists and/or Hh pathway antagonists, through the use of Hh and/or Hh pathway antagonistic antibodies, etc.), and the like.

In some instances, a subject in need of BMP activation for the treatment of a Hh associated cancer may be treated with a combination therapy of an agent that activates BMP and an agent that disrupts Hh expression. In some instances, a subject in need of BMP activation for the treatment of a Hh associated cancer may be treated with a combination therapy of an agent that activates BMP signaling and an agent that disrupts Hh function, e.g., a Hh antagonist. Cancers characterized by repression of BMP signaling, in some instances, are Hh associated cancers. As a non-limiting example, BMP repression, e.g., through cancer cell mediated expression of endogenous BMP antagonists, is a characteristic of BCC as described in, e.g., Sneddon et al. (2006) *PNAS*. 103(40): 14842-14847, the disclosure of which is incorporated herein by reference.

Hh antagonists useful as an additional agent as described herein include but are not limited to, e.g., Hh antagonists that target smoothened (SMO), Hh antagonists that target patched (PTCH), Hh antagonists that target Gli, cyclopamine and analogs and derivatives thereof, cyclopamine-competative antagonists, IPI-926 (Saridegib), LDE225 (sonidegib), itraconazole, GDC-0449 (vismodegib), LEQ506, PF-04449913, TAK-441, BMS833923 (XL-139), LY2940680, and inhibitory nucleic acids targeting SMO, inhibitory nucleic acids targeting a Hh, inhibitory nucleic acids targeting PTCH, inhibitory nucleic acids targeting Gli (e.g., siRNA targeting Gli1), arsenic trioxide, and those described in, e.g., U.S. Pat. App. Publications Nos. 20140018368, 20130296333, 20130274233, 20130190350, 20130012513, 20130011853, 20120316174, 20120309730, 20120283258, 20120238500, 20120183603, 20110263602, 20110190304, 20100098624, 20090156611, 20090130091, 20080058298, 20070232661, 20050256076, 20040110663, 20030166543, 20020015702, and the like.

In some instances, a Hh antagonist useful as an additional agent or a combination of additional agents as described herein may be a non-SMO-related antagonist, e.g., an antagonist that does not function through the direct targeting of SMO or does not function by directly binding SMO. In some instances, non-SMO-related antagonists include but are not limited to, e.g., arsenic and arsenic containing compounds, i.e. arsenicals, and derivatives thereof that inhibit Hh signaling. Certain arsenicals inhibit Hh signaling through the inhibition of Gli signaling, e.g., through inhibition of a Gli or reducing the stability of a Gli. Arsenicals useful in practicing the methods described herein include but are not limited to, e.g., arsenic, sodium arsenite, arsenic trioxide, phenylarsine oxide, combinations thereof, those described in, e.g., Kim et al. (2013) *Cancer Cell*. 23(1)23-34 and Kim et al. (2010) *PNAS*. 107(30)13432-7, the disclosures of which are incorporated herein by reference, and the like.

In some instances, a subject in need of BMP activation for the treatment of a Hh associated cancer may be treated with an agent that activates BMP and may also be treated by activation of Hh signaling, e.g., through increasing or activating or stabilizing a Hh, e.g., by promoting Hh mRNA expression or promoting Hh protein expression, or by increasing or activating or stabilizing a gene or gene product that promotes Hh signaling or by inhibiting or repressing a gene or gene product that inhibits Hh signaling. Increasing Hh and/or activation of Hh signaling in a subject may be achieved by any convenient method including but not limited to, e.g., increasing of Hh expression (e.g., by altering the Hh genomic locus, by altering the locus of Hh repressive genes, through the use of interfering nucleic acids targeting Hh repressive components of the Hh pathway, etc.), activation of Hh pathway component function (e.g., through the use of small molecule Hh agonists and/or Hh pathway agonists, through the use of peptide or polypeptide Hh agonists and/or Hh pathway agonists, through the use of Hh and/or Hh pathway agonistic antibodies, etc.), through direct supplementation of Hh polypeptide or fragments thereof (e.g., including naturally occurring Hh peptide or synthetic Hh peptide or fragments thereof, etc.), through indirect supplementation of Hh polypeptide or fragments thereof (e.g., by providing nucleic acids that encode for Hh polypeptides, Hh-like polypeptides, or fragments thereof, etc.) and the like.

In some instances, a subject in need of BMP activation for the treatment of a Hh associated cancer may be treated with a combination therapy of an agent that activates BMP and an agent that promotes Hh signaling. In some instances, a subject in need of BMP activation for the treatment of a Hh associated cancer or the treatment of a cancer that therapeutically responds to Hh activation may be treated with a combination therapy of an agent that activates BMP signaling and an agent that promotes Hh function, e.g., a Hh agonist. Hh agonists useful as additional agents as described herein include but are not limited to agents that directly affect Hh signaling through interaction with one or more members of the Hh signaling pathway including, e.g., Hh agonists that target SMO. Exemplary Hh agonists include but are not limited to, e.g., benzothiophene smoothened agonists, SAG (Hh-Ag1.3), SAG21k, purmorphamine, those agents and methods of derivation described in, e.g., Chen et al. (2002) *PNAS*. 99(22):14071-14076; Frank-Kamenetsky, et al. (2002) *J Biol*. 1(2):10; Paladini et al. (2005) *J Invest Dermatol*. 125(4):638-46; Nakamura et al. (2014) *J Cell. Physiol*. ePub; U.S. Pat. Nos. 8,852,937; 7,479,539; 7,115,653; 6,683,192; 6,683,108; 6,639,051; 6,613,798, U.S. Patent Application Pub. Nos: 20130085096; 20120238500; 20120148549; 20100183560; 20080207740; 20080171328; 20070110698; 20050112125; 20050070578; 20050054568; 20050014796; 20030139457; 20030022819; 20020198236, and the like.

The terms "co-administration" and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

In some instances, agents useful in co-administration as described herein are agents used in conventional treatment of one or more of the cancers described herein. Such agents include but are not limited to e.g., conventional agents for treating cancer (e.g., chemotherapy agents), hormone agents (e.g., hormone therapy agents conventionally used for treating breast cancer, hormone therapy agents conventionally used for treating prostate cancer, etc.), agents for treating side effects of cancer therapy (e.g., analgesics, anti-nausea agents (e.g., corticosteroids, serotonin antagonists, dopamine antagonists, NK-1 inhibitors, cannabinoids, motion-sickness agents, sedatives, histamine H2-receptor antagonists, etc.), anti-neutropenia agents (e.g., antibiotics, antifungals, granulocyte colony-stimulating factors (G-CSFs), etc.)) agents for treating symptoms of a particular cancer or tumor, and the like. Additional agents useful in co-administration also include agents useful in treating or preventing conditions associated with radiation therapy.

In some instances, treatment of subject having a Hh associated cancer with an agent that activates BMP signaling as described herein includes the administration of a modulator of Hh signaling, including e.g., administration of a Hh antagonist or administration of a Hh agonist. An agent that activates BMP signaling may be administered before, during or after an agent that modulates Hh signaling. In some instances, an agent that activates BMP signaling may be administered after an agent that inhibits Hh signaling. In some instances, an agent that activates BMP signaling is administered with a Hh antagonist to treat a cancer in which Hh signaling promotes carcinogenesis. In some instances, an agent that activates BMP signaling is administered with a Hh antagonist to treat a cancer in which Hh signaling promotes cancer progression. In some instances, an agent that activates BMP signaling is administered with a Hh agonist to treat a cancer in which Hh signaling represses carcinogenesis. In some instances, an agent that activates BMP signaling is administered with a Hh agonist to treat a cancer in which Hh signaling represses cancer progression.

In some instances combination therapy with an agent that activates BMP signaling and a modulator of Hh signaling is performed according to a predetermined schedule, e.g., based on the progression of dynamic Hh signaling for a particular cancer. For example, in some instances, a predetermined treatment protocol of combination therapy will include early treatment, e.g., treatment of a non-invasive carcinoma, that includes a conservative dose (e.g., relatively a low dose) of an agent that activates BMP signaling and an aggressive dose (e.g., a relatively high dose) of an inhibitor of Hh signaling and late treatment, e.g., treatment of an invasive carcinoma, that includes an aggressive dose (e.g., a relatively high dose) of an agent that activates BMP signaling and a conservative dose (e.g., relatively a low dose) of an inhibitor of Hh signaling. In some instances, an agent that modulates Hh signaling, e.g., a Hh antagonist or Hh agonist, may be administered during the entire course, or essentially the entire course of therapy with an agent that activates BMP signaling.

In some instances, the effective dose of either an agent that activates BMP signaling or a modulator of Hh signaling and/or the protocol for administering such agents will depend on the determined stage of a subject's cancer or tumor (e.g., as determined by conventional means of staging and/or evaluating tumors). In some instances, the effective dose of either an agent that activates BMP signaling or a modulator of Hh signaling, will vary and will be dependent on the measured level of BMP signaling and/or Hh signaling in the subject (e.g., as measured by a conventional assay for BMP signaling and/or Hh signaling).

Subjects in need of treatment according to the methods of treatment as described herein include those subjects having Hh associated cancers and those cancers in which modulation of the Hh pathway is therapeutically effective as described herein. Subject in need of treatment according to the methods of treatment as described herein also include those subjects having BMP associated cancers. BMP associated cancers include those cancers that at some point in the cancer carcinogenesis and/or progression a BMP gene or protein or a BMP pathway gene or protein is expressed or misexpressed, e.g., over expressed or under expressed, and BMP signaling is elevated or repressed as compared to related non-cancerous cells or non-invasive cancerous cells. In some instances, a BMP associated cancer is a cancer in which a BMP or a BMP pathway member is repressed during carcinogenesis, e.g., BMP signaling is inhibited in the cancer forming cell type or the pre-cancerous cell. Non limiting examples of BMP associated cancers where BMP signaling is repressed include but are not limited to, e.g., epithelial derived cancers, including e.g., BCC and bladder cancer, as described herein and in, e.g., Sneddon et al. (2006) *PNAS.* 103(40):14842-14847.

In some instances, a patient may be selected for a treatment as described herein based on a determination made and/or evaluation of the cancer of the subject. For example, a subject may be selected for treatment based on a staging of the cancer of the subject, e.g., based on a determination of the invasiveness of the cancer and/or whether the cancer is of a stage indicative of being invasive. In other instances, a subject may be selected based on an assessment of the expression or lack thereof of one or more genes in cancer cells obtained from the subject, including, e.g., assessment of BMP expression, assessment of Hh expression, etc. For example, in some instances a subject may be selected for treatment based on repressed expression (e.g., as compared to control tissue (including control cancer tissue and/or control healthy tissue) or a healthy or cancerous reference standard, of BMP signaling. In certain instances, a subject may be selected for treatment based on elevated expression (e.g., as compared to control tissue (including control cancer tissue and/or control healthy tissue) or a healthy or cancerous reference standard, of Hh Signaling. In certain instances, a subject may be selected for treatment based on a lack of expression (e.g., as compared to control tissue (including control cancer tissue and/or control healthy tissue) or a healthy or cancerous reference standard, of Hh Signaling. In some instances, a subject may be selected based on a dual-assessment, e.g., an assessment of both BMP signaling and Hh signaling, including e.g., an assessment of repressed BMP signaling and elevated Hh signaling. By "expression" is meant any convenient measure of pathway signaling including, e.g., protein expression, gene expression, and the like.

The route of administration may be selected according to a variety of factors including, but not necessarily limited to, the condition to be treated, the formulation and/or device used, the patient to be treated, and the like. Routes of administration useful in the disclosed methods include but are not limited to oral and parenteral routes, such as intravenous (iv), intraperitoneal (ip), rectal, topical, ophthalmic, nasal, and transdermal. Formulations for these dosage forms are described herein.

An effective amount of a subject compound will depend, at least, on the particular method of use, the subject being treated, the severity of the affliction, and the manner of administration of the therapeutic composition. A "therapeutically effective amount" of a composition is a quantity of a specified compound sufficient to achieve a desired effect in a subject (host) being treated.

Therapeutically effective doses (or growth inhibitory amounts) of a subject compound or pharmaceutical composition can be determined by one of skill in the art, with a goal of achieving local (e.g., tissue) concentrations that are at least as high as the IC50 of an applicable compound disclosed herein.

The specific dose level and frequency of dosage for any particular subject may be varied and will depend upon a variety of factors, including the activity of the subject compound, the metabolic stability and length of action of that compound, the age, body weight, general health, sex and diet of the subject, mode and time of administration, rate of excretion, drug combination, and severity of the condition of the host undergoing therapy.

Pharmaceutical Compositions

A pharmaceutical composition comprising a subject compound may be administered to a patient alone, or in combination with other supplementary active agents. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilisate, tablet, pill, pellet, capsule, powder, syrup, elixir or any other dosage form suitable for administration.

A subject compound may be administered to the host using any convenient means capable of resulting in the desired reduction in disease condition or symptom. Thus, a subject compound can be incorporated into a variety of formulations for therapeutic administration. More particularly, a subject compound can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

Formulations for pharmaceutical compositions are well known in the art. For example, Remington's Pharmaceutical Sciences, by E. W. Martin, Mack Publishing Co., Easton, Pa., 19th Edition, 1995, describes exemplary formulations (and components thereof) suitable for pharmaceutical delivery of disclosed compounds. Pharmaceutical compositions comprising at least one of the subject compounds can be formulated for use in human or veterinary medicine. Particular formulations of a disclosed pharmaceutical composition may depend, for example, on the mode of administration and/or on the location of the infection to be treated. In some embodiments, formulations include a pharmaceutically acceptable carrier in addition to at least one active ingredient, such as a subject compound. In other embodiments, other medicinal or pharmaceutical agents, for example, with similar, related or complementary effects on the affliction being treated can also be included as active ingredients in a pharmaceutical composition.

Pharmaceutically acceptable carriers useful for the disclosed methods and compositions are conventional in the art. The nature of a pharmaceutical carrier will depend on the particular mode of administration being employed. For example, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can optionally contain minor amounts of non-toxic auxiliary substances (e.g., excipients), such as wetting or emulsifying agents, preservatives, and pH buffering agents and the like; for example, sodium acetate or sorbitan monolaurate. Other non-limiting excipients include, nonionic solubilizers, such as cremophor, or proteins, such as human serum albumin or plasma preparations.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

The disclosed pharmaceutical compositions may be formulated as a pharmaceutically acceptable salt of a disclosed compound. Pharmaceutically acceptable salts are non-toxic salts of a free base form of a compound that possesses the desired pharmacological activity of the free base. These salts may be derived from inorganic or organic acids. Non-limiting examples of suitable inorganic acids are hydrochloric acid, nitric acid, hydrobromic acid, sulfuric acid, hydroiodic acid, and phosphoric acid. Non-limiting examples of suitable organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, methyl sulfonic acid, salicylic acid, formic acid, trichloroacetic acid, trifluoroacetic acid, gluconic acid, asparagic acid, aspartic acid, benzenesulfonic acid, p-toluenesulfonic acid, naphthalenesulfonic acid, and the like. Lists of other suitable pharmaceutically acceptable salts are found in Remington's Pharmaceutical Sciences, 17th Edition, Mack Publishing Company, Easton, Pa., 1985. A pharmaceutically acceptable salt may also serve to adjust the osmotic pressure of the composition.

A subject compound can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. Such preparations can be used for oral administration.

A subject compound can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. The preparation may also be emulsified or the active ingredient encapsulated in liposome vehicles. Formulations suitable for injection can be administered by an intravitreal, intraocular, intramuscular, subcutaneous, sublingual, or other route of administration, e.g., injection into the gum tissue or other oral tissue. Such formulations are also suitable for topical administration.

In some embodiments, a subject compound can be delivered by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

A subject compound can be utilized in aerosol formulation to be administered via inhalation. A subject compound can be formulated into pressurized acceptable propellants such as dichlorodifluoromethane, propane, nitrogen and the like.

Furthermore, a subject compound can be made into suppositories by mixing with a variety of bases such as emulsifying bases or water-soluble bases. A subject compound can be administered rectally via a suppository. The suppository can include vehicles such as cocoa butter, carbowaxes and polyethylene glycols, which melt at body temperature, yet are solidified at room temperature.

The term "unit dosage form," as used herein, refers to physically discrete units suitable as unitary dosages for human and animal subjects, each unit containing a predetermined quantity of a subject compound calculated in an amount sufficient to produce the desired effect in association with a pharmaceutically acceptable diluent, carrier or vehicle. The specifications for a subject compound depend on the particular compound employed and the effect to be achieved, and the pharmacodynamics associated with each compound in the host.

The dosage form of a disclosed pharmaceutical composition will be determined by the mode of administration chosen. For example, in addition to injectable fluids, topical or oral dosage forms may be employed. Topical preparations may include eye drops, ointments, sprays and the like. In some instances, a topical preparation of a medicament useful in the methods described herein may include, e.g., an ointment preparation that includes one or more excipients including, e.g., mineral oil, paraffin, propylene carbonate, white petrolatum, white wax and the like, in addition to one or more additional active agents. For example, in some instances a topical preparation, e.g., an ointment, may include an agent that activates BMP signaling, e.g., FK506, or a combination of an agent that activates BMP signaling and an additional active agent, e.g., a Hh modulator, and, optionally, one or more of the above listed excipients. The amount of an active agent in an topical preparation may vary and in some instances may include a concentration ranging from 0.001% to 10% active agent, including but not limited to, e.g., 0.001%, to 0.005%, 0.001% to 0.01%, 0.001% to 0.02%, 0.001% to 0.025%, 0.001% to 0.03%, 0.001%, to 0.04%, 0.001%, to 0.05%, 0.001%, to 0.06%, 0.001%, to 0.07%, 0.001%, to 0.08%, 0.001%, to 0.09%, 0.001%, to 0.1%, 0.001%, to 1%, 0.01%, to 0.1%, 0.01%, to 1%, 0.1% to 1%, 0.001%, 0.002%, 0.003%, 0.004%, 0.005%, 0.006%, 0.007%, 0.008%, 0.009%, 0.01%, 0.011%, 0.012%, 0.013%, 0.014%, 0.015%, 0.016%, 0.017%, 0.018%, 0.019%, 0.02%, 0.025%, 0.03%, 0.035%, 0.04%, 0.045%, 0.05%, 0.055%, 0.06%, 0.065%, 0.07%, 0.075%, 0.08%, 0.085%, 0.09%, 0.095%, 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, and the like. Oral formulations may be liquid (e.g., syrups, solutions or suspensions), or solid (e.g., powders, pills, tablets, or capsules). Methods of preparing such dosage forms are known, or will be apparent, to those skilled in the art.

Certain embodiments of the pharmaceutical compositions comprising a subject compound may be formulated in unit dosage form suitable for individual administration of precise dosages. The amount of active ingredient administered will depend on the subject being treated, the severity of the affliction, and the manner of administration, and is known to those skilled in the art. Within these bounds, the formulation to be administered will contain a quantity of the extracts or compounds disclosed herein in an amount effective to achieve the desired effect in the subject being treated.

Each therapeutic compound can independently be in any dosage form, such as those described herein, and can also be administered in various ways, as described herein. For example, the compounds may be formulated together, in a single dosage unit (that is, combined together in one form such as capsule, tablet, powder, or liquid, etc.) as a combination product. Alternatively, when not formulated together in a single dosage unit, an individual subject compound may be administered at the same time as another therapeutic compound or sequentially, in any order thereof.

In certain embodiments, the method includes treating a subject for cancer, the method comprising administering to the subject a composition comprising a therapeutically effective amount of an agent that activates BMP signaling and a therapeutically effective amount of a modulator of Hh signaling, wherein the agent that activates BMP signaling is FK506 or an analog thereof.

In certain embodiments, the method includes treating a subject for cancer, the method comprising administering to the subject a composition comprising a therapeutically effective amount of FK506 or an analog thereof and a therapeutically effective amount of a modulator of Hh signaling, wherein FK506 is administered to the subject at a low dose effective to avoid immunosuppression.

In certain embodiments, the method includes treating a subject for cancer, the method comprising administering to the subject a composition comprising a therapeutically effective amount of an agent that activates BMP signaling and a therapeutically effective amount of a Hh antagonist.

In certain embodiments, the method includes treating a subject for cancer, the method comprising administering to the subject a composition comprising a therapeutically effective amount of an agent that activates BMP signaling and a therapeutically effective amount of a Hh agonist.

Kits

Also provided are kits for use in the subject methods. The subject kits include any combination of components and compositions for performing the subject methods. In some embodiments, a kit can include the following: an agent that activates BMP signaling, any additional agent as described herein, a pharmaceutical application device or delivery device; and any combination thereof.

In some embodiments, a subject kit includes an agent that activates BMP signaling (e.g., FK506) and a Hh antagonist. In some instances, a subject kit includes an agent that activates BMP signaling and an excipient for delivering the agent, e.g., in separate tubes. In some instances, a subject kit may include metered doses of an agent that activates BMP signaling and/or metered doses of an additional agent, e.g., a Hh antagonist or a Hh agonist, e.g., that may represent a treatment regimen. In instances where topical delivery is indicated, a subject kit may include one or more compositions or devices for the topical administration of an agent that activates BMP signaling and/or a Hh antagonist or a Hh agonist.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., room temperature (RT); base pairs (bp); kilobases (kb); picoliters (pl); seconds (s or sec); minutes (m or min); hours (h or hr); days (d); weeks (wk or wks); nanoliters (nl); microliters (ul); milliliters (ml); liters (L); nanograms (ng); micrograms (ug); milligrams (mg); grams ((g), in the context of mass); kilograms (kg); equivalents of the force of gravity ((g), in the context of centrifugation); nanomolar (nM); micromolar (uM), millimolar (mM); molar (M); amino acids (aa); kilobases (kb); base pairs (bp); nucleotides (nt); intramuscular (i.m.); intraperitoneal (i.p.); subcutaneous (s.c.); and the like.

Example 1

Protective Effect of Stromal Response to Hedgehog Signaling in Bladder Cancer

To elucidate the role of Hh signaling in bladder carcinogenesis, we have examined Shh expression and signaling in benign and malignant human bladder and have investigated the role and mechanism of Hh signaling in the murine invasive bladder cancer model. We present evidence that progression of urothelial carcinoma in mice is associated with loss of Hedgehog signaling, and consequent loss of BMP signaling. We further show that BMP pathway activation by treatment with low-dose FK506 halts progression of bladder cancer in mice.

Absence of SHH Expression in Human Invasive Urothelial Carcinoma

Figure 8A:
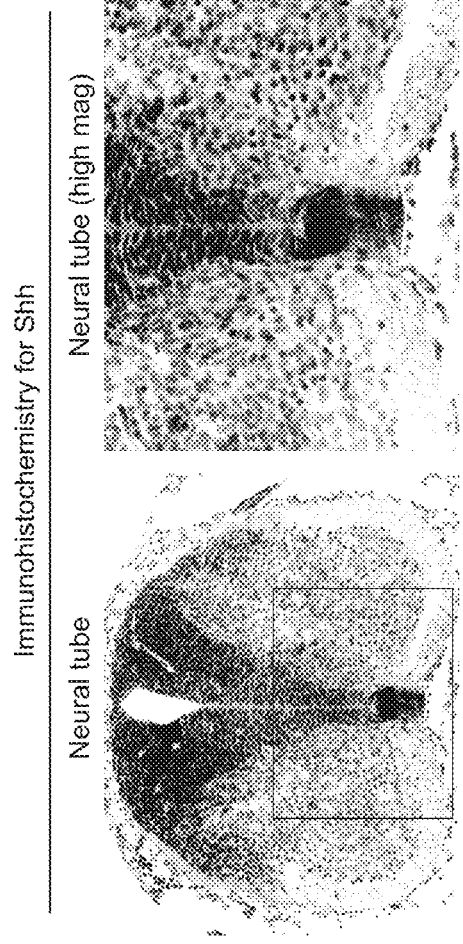
FIGS. 8A-8B. Immunohistochemistry to detect the expression of Shh in the human bladder.
Figure 8B:
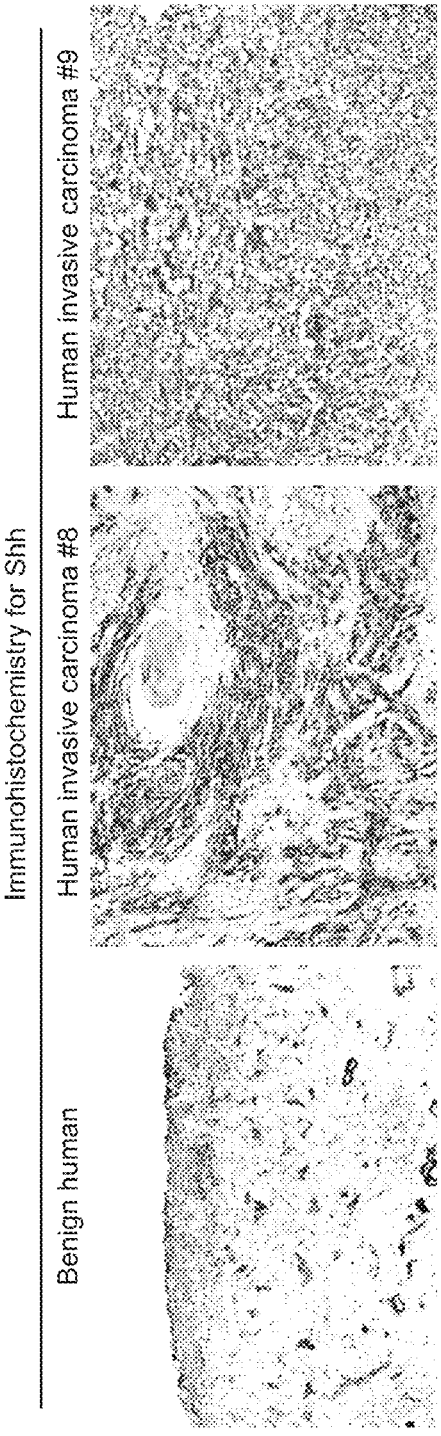

Having previously established the absence of Shh expression in murine invasive urothelial carcinoma[6], we compared the expression of SHH mRNA in human benign urothelium with muscle-invasive urothelial carcinoma samples, with histological confirmation by H&E staining of tissue sections (FIG. 7A-7B). We found that all three invasive carcinoma samples examined showed a marked decrease in SHH expression (FIG. 1A), consistent with our previous work in murine invasive urothelial carcinoma and a previous RT-PCR analysis of human urothelial cell carcinomas at advanced stages, which also showed low or undetectable expression of SHH mRNA[13,14]. To confirm and extend these results, we performed immunohistochemistry (IHC) for the expression of Shh protein in human invasive urothelial carcinoma samples (FIGS. 1B-1C and FIG. 8B) using an antibody that specifically detects Shh, as validated by IHC of murine tissues in which the expression pattern of Shh is known[12] (FIG. 8A). We found high levels of Shh protein in human benign bladder urothelium (FIG. 1B and FIG. 8B), but little if any detectable Shh in the primary cancer cells of all six invasive carcinomas examined (FIG. 1C and FIG. 8B). We note that IHC revealed Shh reactivity within the tumor fibrovascular cores but absent in the lining carcinoma cells, and this may account for the low level of SHH mRNA detected in the carcinoma samples by RT-PCR.

Genetic Ablation of Hh Response Accelerates Bladder Carcinogenesis

Given the consistent absence of SHH expression in invasive urothelial carcinoma, we considered the possibility that loss of Hh signaling may accelerate tumor growth and progression. To test this possibility, we exposed mice to drinking water containing BBN, a procarcinogen that induces advanced bladder cancer in many experimental animals[15-17]; nitrosamines are potent carcinogens present in cigarette smoke, which is the most important risk factor in human bladder cancer. In our previous work, BBN exposure reliably induced a pre-malignant lesion histologically indistinguishable from human urothelial carcinoma in situ (CIS) by 3-4 months of exposure, with invasive carcinoma developing by 5-6 months[6]. With no prior bias regarding genetic pathway or cell type, BBN exposure thus provides a clinically relevant experimental model of human bladder carcinogenesis with a defined course of progression to invasive carcinoma. The use of chemical carcinogenesis in this model previously permitted the use of genetic methods to establish the Shh-expressing basal stem cell as the cancer cell of origin and to investigate the tissue dynamics of invasive bladder cancer progression[6]; here we use genetic methods to probe the role of Hh signaling during carcinogenesis.

Figure 2B:
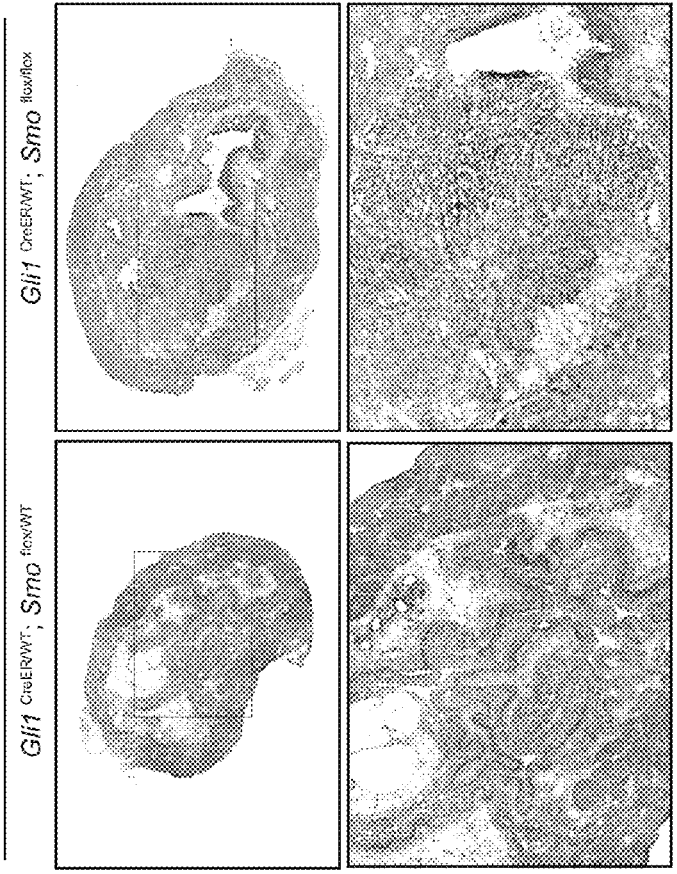

We previously established that Shh expression occurs constitutively in basal cells of the urothelium and that response, as manifested by low-level expression of Gli1, is restricted to stromal cells[2]. To genetically inactivate stromal Hh response, we injected tamoxifen (TM) into mice expressing CreER under control of the Gli1 promoter and carrying homozygous floxed alleles of the essential Hh pathway transductory component smoothened (Smo) (Gli1$^{CreER}$; Smo flox/flox). This treatment will block Hh response in stromal cells undergoing Hh response under baseline conditions, prior to BBN exposure. In mice thus treated, we found that tumors appeared as early as 3 months after initiation of BBN exposure, a time at which control animals were just beginning to develop CIS-like lesions (FIG. 2A). Furthermore, these mice survived a median of 140 days, as compared to 215 days for Smo heterozygous control animals (FIG. 2B), a reduction of 35%. This dramatic reduction in survival indicates that genetic ablation of Hh response in bladder stroma significantly accelerates the progression of BBN-induced bladder cancer. If general loss of stromal Hh response accelerates cancer growth, the loss of Shh expression from pre-malignant cells in a CIS lesion may confer a local growth advantage by reducing Hh pathway activity in neighboring stroma, ultimately leading to preferential expansion of such clones of cells during progression to advanced invasive urothelial carcinomas. Such preferential expansion could account for the prevalence of invasive carcinomas lacking Shh expression.

Reduced Expression of Differentiation Factors in Smo-Ablated Mice

Figure 9A:
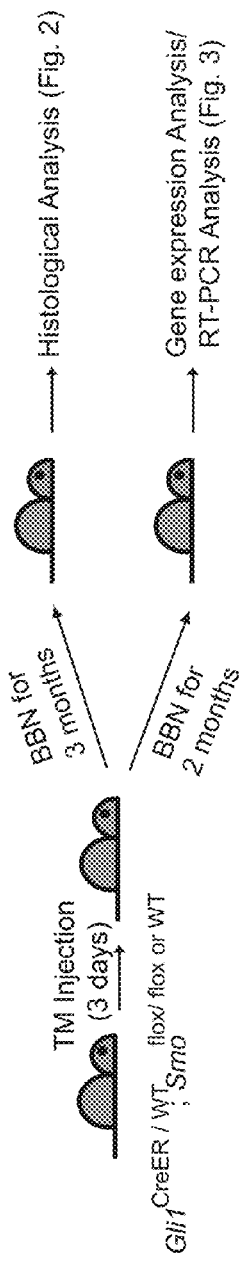
FIGS. 9A-9B. Decreased cellular differentiation in Smo-ablated bladders.
Figure 9B:
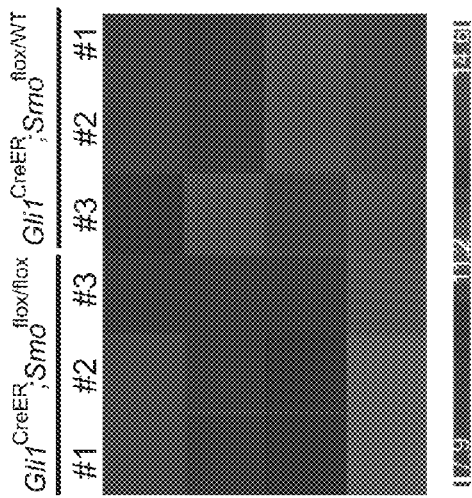

The consistent loss or attenuation of Shh expression in the latter stages of tumor progression and the experimental acceleration of tumor progression with genetic ablation of Smo function in Hh-responsive stromal cells together suggest that secreted stromal factors induced by Hh signaling hinder the formation of aggressive tumors. To identify Hh-regulated molecular pathways involved in delaying tumor formation, we performed gene expression profiling on bladder samples from Gli1$^{CreER}$; Smo$^{flox/flox}$ and Gli1$^{CreER}$; Smo$^{flox/WT}$ mice. Following TM injection, mice were exposed to BBN for 2 months prior to gene expression analyses (FIG. 9A). The 2-month time point was chosen in order to detect molecular changes that are present very early in the tumor formation process, before overt histological differences can be seen, as these early molecular changes are likely to drive the cellular processes responsible for later phenotypic differences. Indeed, mice of both genotypes were histologically identical at this 2-month time point (data not shown).

Figure 3A:
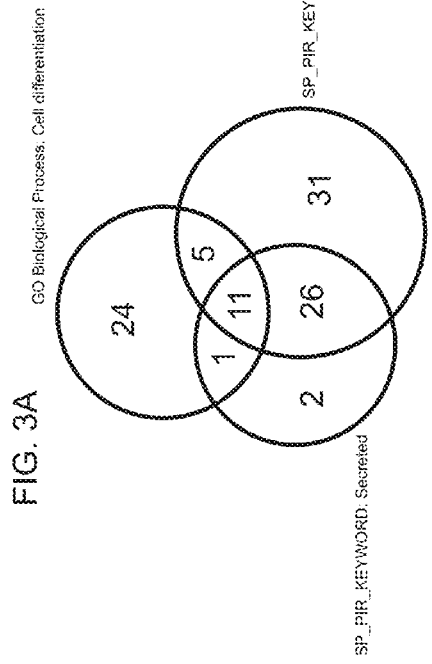
FIGS. 3A-3C. Reduced expression of differentiation factors in Smo-ablated mice.

Comparison of the gene expression profiles revealed that 468 genes were at least 2-fold down-regulated in bladder samples from Gfi$^{CreER}$; Smo$^{flox/flox}$ mice exposed to BBN (p<0.01); gene ontology analysis indicated an enrichment of genes involved in developmental processes and cell differentiation in this list (Table 1). The apparent down-regulation of cell differentiation genes in TM-treated Gli1$^{CreER}$; Smo$^{flox/flox}$ mice suggests the possibility that accelerated cancer progression with loss of Hh pathway activity is due to decreased expression of differentiation-promoting factors that may increase the pool of primitive cells with the potential to progress to invasive carcinoma. Supporting this hypothesis, we found that Uroplakin gene expression, which is indicative of urothelial differentiation, is significantly decreased in Smo-ablated mouse bladders (Supplementary FIG. 3B). As decreased Hh pathway activity, occurring in stroma, must affect tumor-forming urothelial cells, we focused on those cell differentiation genes (Table 2) that encode secreted proteins involved in cell signaling (FIG. 3A). Bone morphogenic protein 4 (Bmp4) and Bmp5[18] are particularly of interest because: (i) Bmp4 has been shown to promote terminal differentiation of bladder urothelium[19]; (ii) some Bmp genes are known to be directly regulated by the Hh pathway activity[20,21]; and (iii) Bmp signaling plays a role in the differentiation of tissues in other organs such as lungs[22] and heart[23].

Figure 3C:
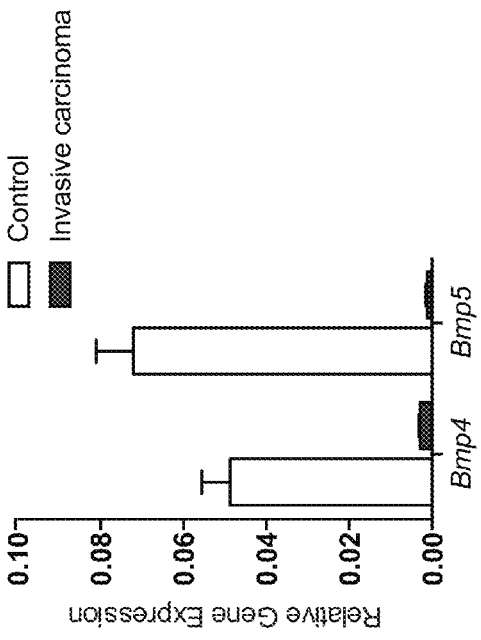
Figure 3B:
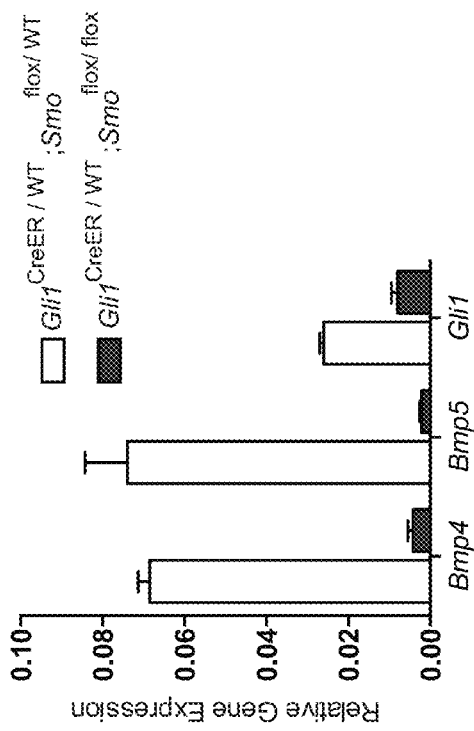

To confirm decreased Bmp4 and Bmp5 expression, we carried out quantitative RT-PCR with samples from the bladders of TM-injected Gli1$^{CreER}$; Smo$^{flox/flox}$ and Gli1$^{CreER}$; Smo$^{flox/WT}$ mice exposed to BBN for 2 months. Attenuation of Hh pathway activity was verified by a reduction in the expression of Gli1, a transcriptional target of the pathway, and this was correlated with a sharp reduction in the levels of Bmp4 and Bmp5 (FIG. 3B). We further examined Bmp4 and Bmp5 mRNA in wild-type mice exposed to BBN for six months and found that expression of Bmp4 and Bmp5 was greatly reduced in invasive carcinoma as compared to control bladders from mice without exposure to BBN (FIG. 3C). These results suggest that decreased Bmp expression resulting from loss of Hh signaling may account for the increased rate of tumor formation observed in mice with ablated Smo function (FIG. 2A).

Stromal Hh Response Regulates Expression of Human BMP4 and BMP5 Genes

Figure 4A:
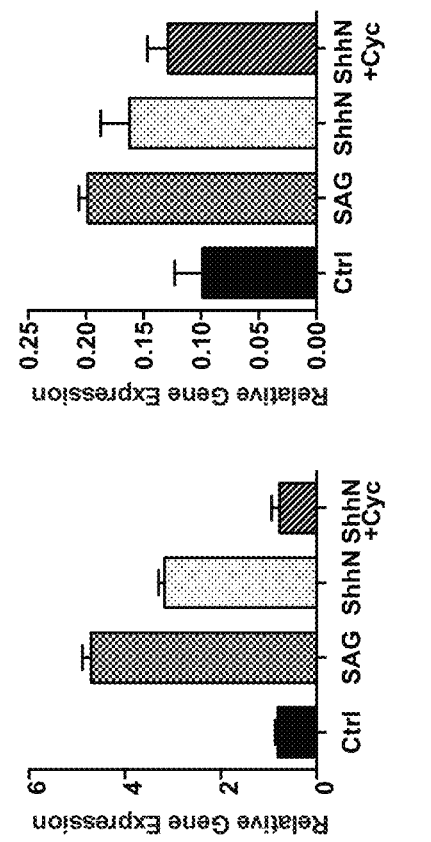
FIGS. 4A-4D. Stromal Hh response regulates expression of human BMP4 and BMP5 genes.
Figure 4B:
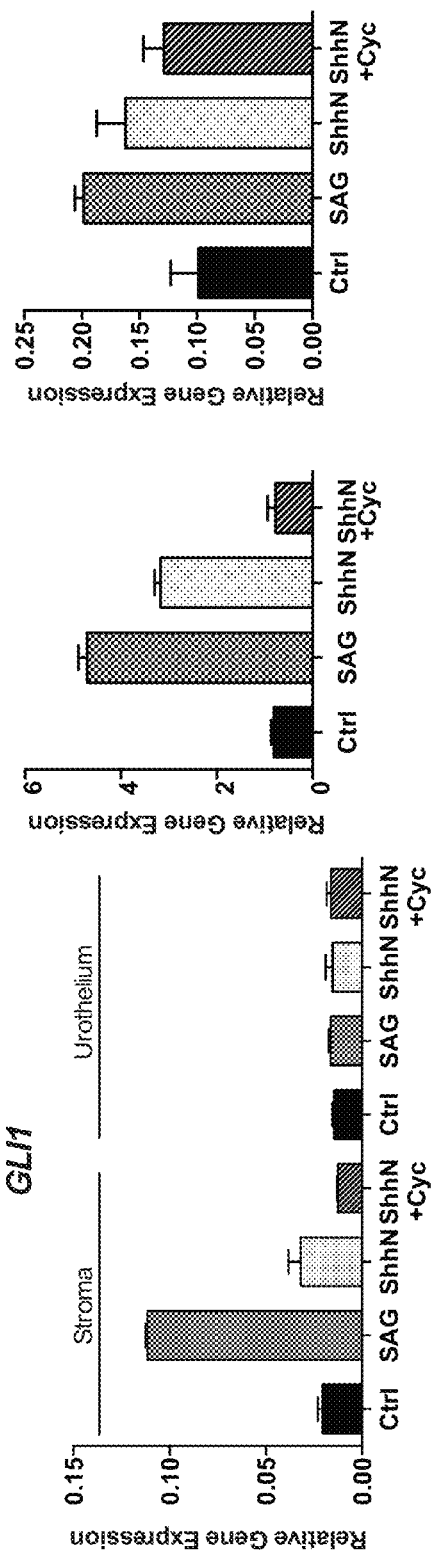
Figure 10:
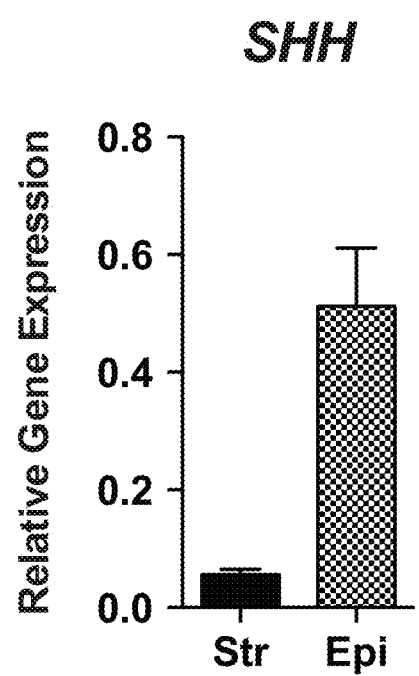
FIG. 10. Human bladder epithelial cells expresses SHH. Expression of SHH in primary human bladder stromal (Str) or urothelial (Epi) cells. SHH is expressed at a high level in urothelial cells.
Figure 11:
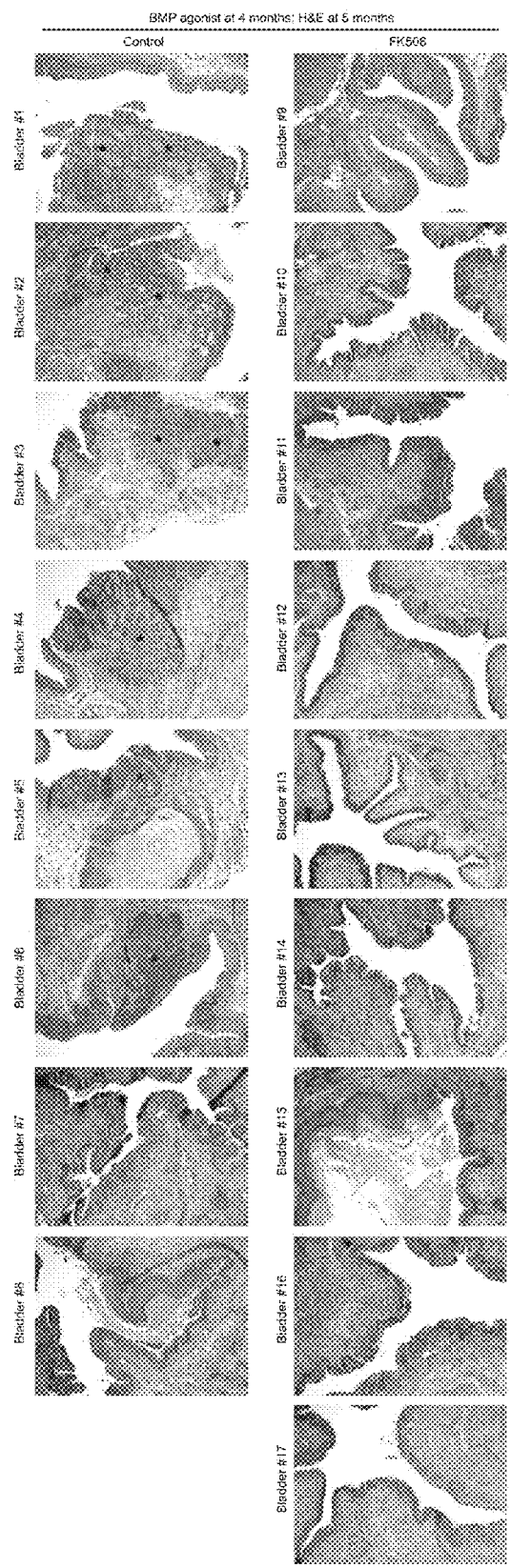
FIG. 11. Pharmacological activation of Bmp signaling in vivo impedes tumor progression to invasive urothelial carcinoma. Hematoxylin and eosin (H&E) stained bladder sections from mice exposed to BBN for 5 months, including 1 month of treatment with FK506 or a vehicle control. Asterisks indicate regions of invasive carcinoma in bladder samples #1-6.

To determine whether Hh signaling regulates expression of BMP4 and BMP5 in human bladder, we first examined the expression of Hh pathway components in primary human bladder fibroblasts and epithelial cells. Consistent with immunostaining for Shh using benign bladder sections (FIG. 1B, FIG. 8B), we found that SHH is expressed in primary cultures of bladder urothelial cells (FIG. 10), consistent with our findings in mouse. To evaluate response to the Hh signal, we treated cultured human bladder stromal and urothelial cells with ShhN protein or with the chemical pathway agonist SAG[24]. Hh pathway activation, as judged by an increase in GLI1 expression, only occurred in cultured stromal cells (FIG. 4A), and this effect was reversed by addition of the pathway antagonist cyclopamine[25,26], suggesting that Hh signaling in human bladder mirrors that in the mouse, with epithelial expression of Hh ligand and signal response restricted to stroma[2]. Concomitant with the increase in GLI1 mRNA upon stimulation of the cultured human bladder stromal fibroblasts, we noted an increase in levels of BMP4 and BMP5 transcripts (FIG. 4B). These data suggest that stromal cells in human bladder, like those in the mouse, respond to Hh ligand stimulation with increased transcription of BMP4 and BMP5.

Figure 4C:
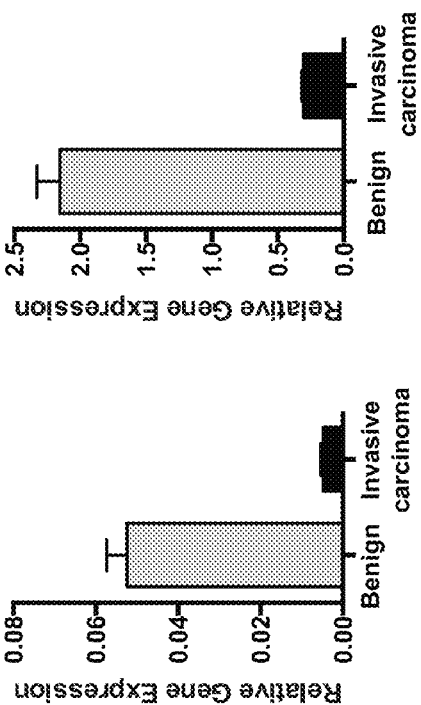
Figure 4D:
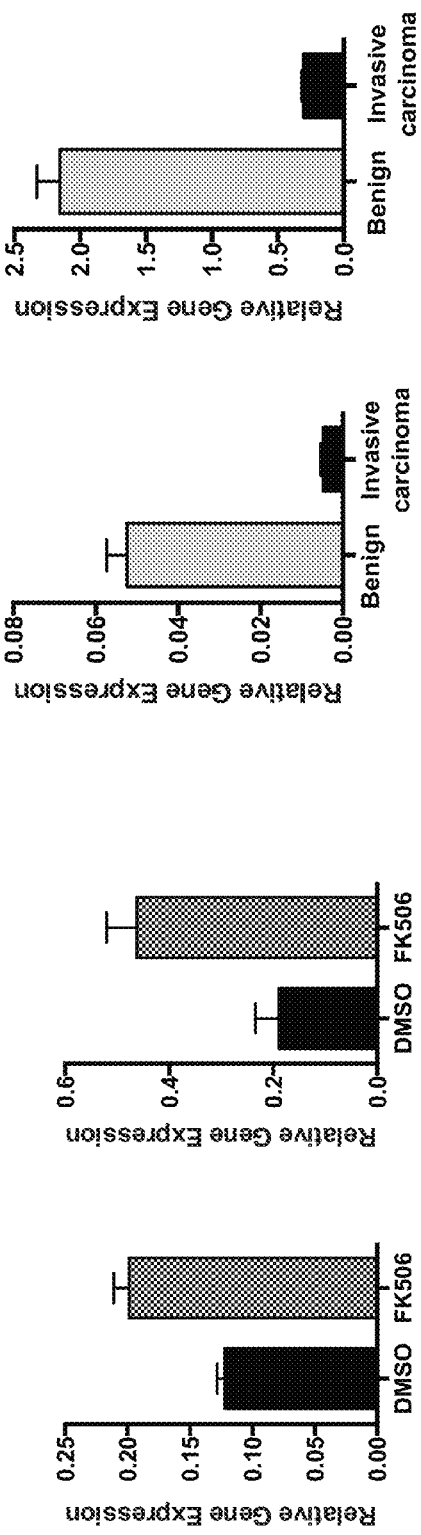

As Bmp4 and Bmp5 secreted from stromal cells have the potential to act on urothelium, we tested the ability of cultured urothelial cells to respond to BMP pathway activation. For this purpose we selected FK506, an FDA-approved drug recently shown to activate BMP pathway at concentrations below those required for its immunosuppressant effects[27]. Treatment of cultured urothelial cells with FK506 induced expression of BMP target genes ID4[28,29] and CDKN1B[19,30,31] (FIG. 4C), suggesting a reciprocal epithelial-stromal signal feedback loop in which Shh secreted by the urothelium activates Hh response in bladder stromal cells, resulting in stromal expression of BMP4 and BMP5 that in turn signals back to the urothelium. Loss of Shh expression in human invasive carcinomas, as noted previously (FIG. 1A), would be expected to disrupt this signal feedback; this expectation was confirmed by a dramatic reduction of BMP4 and BMP5 expression in human invasive urothelial carcinoma as compared to benign bladder (FIG. 4D).

Pharmacological Activation of the Bmp Pathway Impedes Tumor Progression

To investigate the role of Bmp pathway activity in bladder tumor progression and to test the possibility that Bmp pathway activation might stimulate urothelial differentiation, which in turn might impede tumor progression, we exposed mice to BBN for 4 months, then initiated treatment with FK506 for another month while also continuing exposure to BBN (FIG. 5A). We have previously noted that mice exposed to BBN for 4 months develop pre-malignant lesions indistinguishable from human carcinoma-in-situ but not invasive carcinoma, which requires further BBN exposure[6]. In our control group, continuation of BBN exposure for a total of five months resulted in the development of invasive carcinoma in 7 of 9 mice. For the cohort of 10 mice treated with FK506 during the final month, however, no invasive carcinoma was observed, suggesting that activation of Bmp pathway activity may impede progression if treatment occurs prior to formation of invasive carcinoma.

Figure 6:
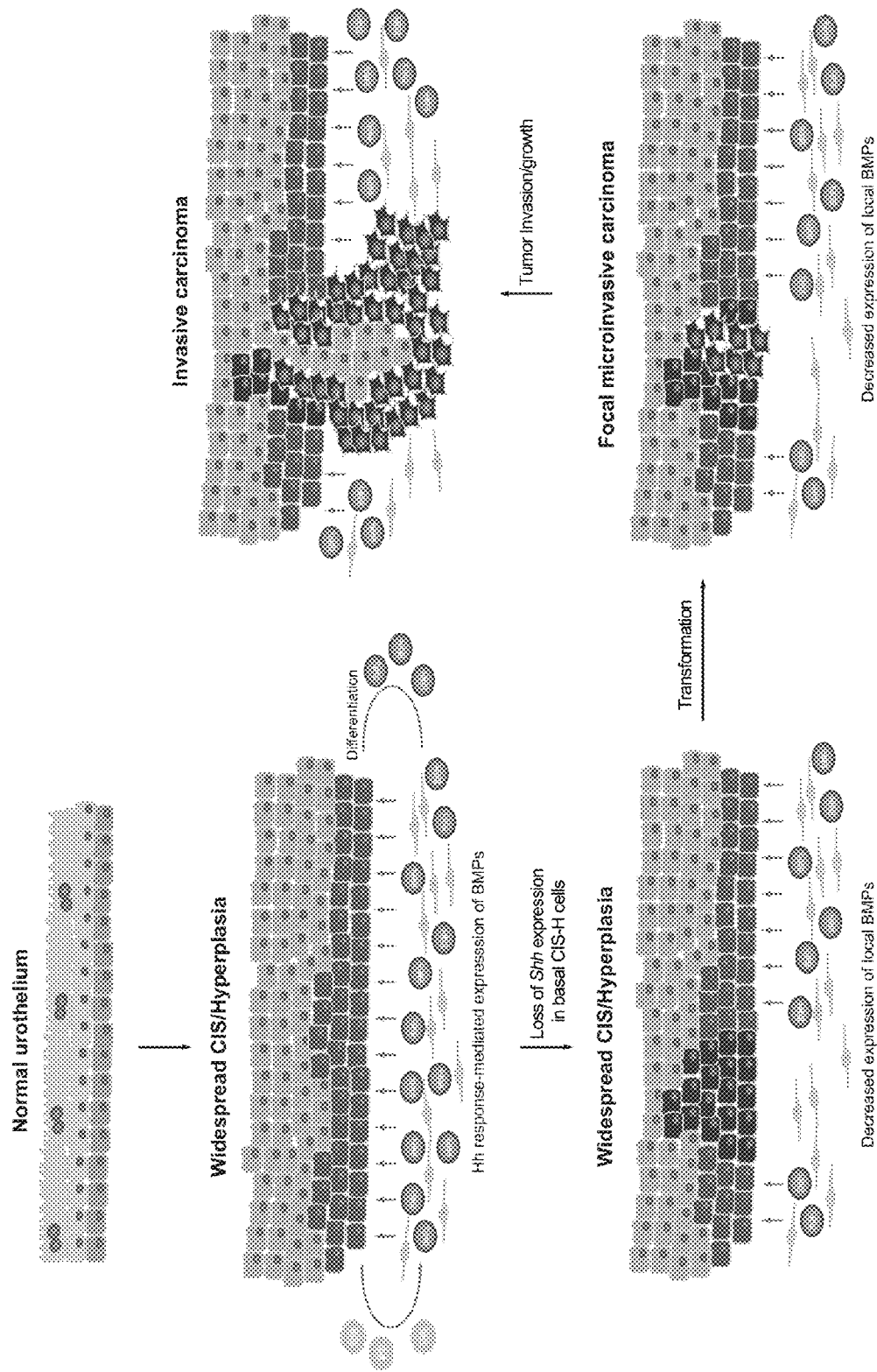
FIG. 6. Model of the protective effect of stromal Hh response in bladder cancer progression. Following formation of a precursor lesion (red and pink cells), loss of Shh expression (brown cells) in the precursor lesion leads to decreased expression of Hh-inducible stromal differentiation factors (BMPs) locally, resulting in increased numbers of undifferentiated pre-malignant cells with proliferative advantages. Once transformed, these cells can then initiate focal invasive behavior, as they fail to elicit Hh-inducible stromal differentiation factors (BMPs) locally while maintaining proliferative capacity. This proliferative advantage during progression to invasion results in selection of Shh-negative invasive carcinoma.

Our observations together support the model in FIG. 6, in which progression of CIS to invasive carcinoma is triggered by loss of Hh signaling. This idea is strongly supported by the observed loss of Shh expression in both murine and human invasive urothelial carcinomas[6] (see FIGS. 1A-1C), and by the dramatically accelerated progression to invasive urothelial carcinoma observed with BBN exposure when stromal response to Shh signaling is experimentally ablated (see FIGS. 2A-2B). The role of BMPs as mediators of this effect is suggested by Shh-dependent expression of BMP4 and BMP5 in both murine and human stromal cells (FIGS. 3A-3C, FIGS. 4A-4D), and by the dramatically delayed progression to invasive carcinoma upon treatment with a BMP pathway agonist (FIGS. 5A-5C). We propose that this delay of progression is likely due to induction of urothelial cell differentiation by BMP pathway activity[19]; such activity is present in benign tissues and at early stages of tumor development because of stromal response to Shh from the urothelium. The local reduction or loss of this differentiation-inducing activity upon loss of urothelial Shh in cells of a nascent micro-invasion might then permit tumor cells to continue to grow and advance, leading ultimately to invasive carcinoma.

Discussion

The discovery of cyclopamine and synthetic mimics as Hh inhibitors that act by binding the essential pathway component smoothened (Smo)[25,26] has led to the development of potent Smo antagonists as therapeutic agents. One of these, Vismodegib, has been approved by the FDA for systemic use in patients with metastatic or locally advanced basal cell carcinoma[32-34], and promising early results with this and other Hh inhibitors have been reported in clinical trials in medulloblastoma[35] and acute myelogenous leukemia[36]. These drugs, however, have not shown clinical benefit in trials of pancreatic, colon, or ovarian cancers[34,37-39]. The pancreatic cancer trial results in particular have been puzzling, as preclinical studies in mice with xenografted or autochthonous tumors appeared promising[10,11], but the clinical trials had to be halted due to accelerated cancer progression[34,39].

Our previous work demonstrated that Shh produced in basal stem cells of the murine urothelium elicits proliferative Wnt and FGF signals from underlying stroma during injury-induced regeneration[2], and we consequently expected Hh pathway activity to favor bladder neoplasia. To our surprise, however, in the murine BBN model Shh expression is invariably lost during progression to invasive carcinoma, despite its early presence in the basal urothelial cell of origin and in CIS-like intermediate lesions[6]. This loss of Shh expression led us to question the role of Hh pathway activity in advanced bladder cancer. Indeed, we find that Hh pathway activity actually protects against rather than stimulates cancer progression, as development of invasive urothelial carcinoma is dramatically accelerated by genetic ablation of the stromal response to Shh signaling in the murine BBN model. Expression profiling at early stages of BBN exposure identified BMP4 and BMP5 proteins as Hh-induced factors that are secreted by stromal cells. As BMP signaling is known to foster differentiation of urothelial cells[19], BMP pathway activity might reverse or attenuate the proliferative state of relatively undifferentiated urothelial carcinoma cells. Such a protective role for BMP activity is strongly supported by the dramatic effect of a BMP pathway agonist that we observed to dramatically impede progression of CIS-like intermediate lesions to fully invasive urothelial carcinoma.

Our studies in human bladder cells and bladder cancer samples confirm: (i) that SHH is normally made in urothelium; (ii) that Hh pathway activity induces BMP4 and BMP5 expression in stromal cells; and (iii) that SHH, BMP4, and BMP5 expression are lost in invasive carcinoma. These observations suggest that mechanisms similar to those characterized in the murine BBN model may also operate in human bladder cancer progression. The BMP agonist used in our murine BBN model, FK506, has long been in clinical use as an immunosuppressant[40]. Concentrations and doses of FK506 like those used here, however, have been shown to activate BMP pathway activity without causing immunosuppression[27], raising the possibility that low-dose FK506 therapy may have utility in halting or slowing progression of human bladder cancer. Such treatment could have a significant impact in clinical management of bladder cancer, as high rates of progression and recurrence make treatment of this cancer more costly than any other on a per patient basis[41].

The protective effect of Hh pathway activity in cancer of the urinary bladder, an organ of endodermal origin, may relate to the negative outcomes of Hh inhibitor trials in other malignancies of endodermal organs. In particular, the accelerated progression of pancreas cancer upon pharmacological blockade with Smo antagonists could involve a similar effect to that seen with genetic blockade by Smo ablation in our murine BBN model. We note that Shh expression in human exocrine pancreas also occurs in the epithelium, and that signal response is also restricted to stroma[42]. This stromal response includes expression of Wnt and other proliferative signals, but may also include expression of differentiation-inducing factors as seen in bladder. If stromal cells of various organs can produce factors that stimulate both epithelial differentiation and proliferation, the question arises as to the circumstances under which differentiation or proliferation may prevail. We know in the bladder that balanced production of proliferation and differentiation-inducing stromal signals is critical to regeneration of normal urothelium[2], but it seems that during cancer progression the differentiation-inducing activity gains in importance, and helps keep the tumor in check. One possible explanation for this shift is that in early stages of cancer development, cells of nascent epithelial cancers may acquire reduced dependence on proliferative stromal factors through genetic or epigenetic changes that generate cell-autonomous proliferative drive, while leaving cells sensitive to the effects of differentiation-inducing factors; in this circumstance, cancer progression may be triggered by loss of the production or the response to such differentiation-inducing factors. In the bladder Shh from the urothelium induces both types of stromal signals. If epithelial Hh signaling to stroma similarly induces such balanced responses in other organs, an understanding of the impact that activation or inhibition of Hh pathway activity may have requires an understanding of both normal homeostasis as well as the derangements associated with carcinogenesis.

Methods Summary

For BBN-induced bladder carcinogenesis, a 0.1% concentration of BBN was provided to mice ad libitum for 4-6 months. For Smo deletion experiments, a transgene expressing tamoxifen-activated Cre was used to selectively inactivate a conditional allele of Smo. To activate the BMP pathway, Alzet osmotic pumps were implanted subcutaneously to administer FK506 to mice exposed to BBN. Quantitative RT-PCR was used for measurement of RNA levels in samples isolated from the human and mouse bladder samples. For in vitro cultures, primary human bladder urothelial and stromal cells were treated with FK506 for 12 hours, or serum-starved and treated with SAG or Shh conditioned medium with or without cyclopamine for 24 hours prior to gene expression analyses.

Methods

Mice

For Smo deletion experiments, $Gli1^{CreER/WT}$ mice were mated with the $Smo^{flox/flox}$[43,44] strain to obtain $Gli1^{CreER}$; $Smo^{flox/flox}$ and $Gli^{CreER}$; $Smo^{flox/WT}$ mice, which were injected intraperitoneally with 4 mg of TM (per 30 g body weight) daily for three consecutive days prior to BBN exposure. All mouse strains were obtained from Jackson Laboratories. Mouse procedures were performed under isoflurane anesthesia, which was administered in a fume hood with a standard vaporizer (J. B. Baulch & Associates). All procedures were performed under a protocol approved by the Administrative Panel on Laboratory Animal Care at Stanford University.

BBN-Induced Bladder Carcinogenesis

A 0.1% concentration of BBN (TCI America) was dissolved in drinking water, and BBN-containing water was provided to mice ad libitum for 4-6 months in a dark bottle. BBN-containing water was changed twice a week. Bladders were collected and analyzed after 4 to 6 months of BBN administration.

Human Bladder Tissue Samples

Human bladder tissue samples were collected under protocols approved by Institutional Review Board (IRB) at Stanford University. The bladder tissue samples were obtained and processed within one hour after endoscopic resection or radical cystectomy from patients with confirmed muscle invasive urothelial carcinoma (stage≥pT2). For gene expression analysis, unfixed tissue samples were embedded in optimal cutting temperature (OCT) compound (Tissue-Tek) for snap freezing. For immunohistochemistry, tissue samples were fixed in 4% paraformaldehyde (PFA) overnight at 4° C., followed by dehydrating in 30% sucrose overnight then embedded in OCT compound, and sectioned into 12-micron thick sections with a Microm cryostat.

Immunohistochemistry

Frozen sections of patient bladder tissue samples were air dried for 20 minutes and post-fixed in 4% PFA for 30 minutes. Sections were then blocked for endogenous peroxidase activity for 10 minutes with BLOXALL (Vector Labs) and subsequently incubated with 1.5% goat serum for 30 minutes, followed by incubation with primary rabbit anti-Shh antibody (C9C5, Cell Signaling) overnight. Sections were then incubated with secondary biotinylated goat anti-rabbit antibody (Vector Labs) for 60 minutes, followed by incubation with VECTSTAIN ABC Standard Kit (Rabbit IgG; Vector Labs) for 30 minutes. Sections were developed with ImmPACT DAB peroxidase substrate (Vector Labs) for 1 minute and counter-stained with Hematoxylin QS (Vector Labs). Sections were gradually dehydrated and cleared before mounting with cytoseal 60 (Thermo Scientific).

Histological Analysis

Human or mouse tissue specimens were embedded in OCT compound and sectioned into 12 micron thick sections with a Microm cryostat. Slides were fixed in 4% PFA for 30 min at 4° C., stained with hematoxylin, then counter-stained with Eosin.

Microarray Analysis $Gli1^{CreER}$; $Smo^{flox/flox}$ and $Gli1^{CreER}$; $Smo^{flox/WT}$ mice were injected intraperitoneally with 4 mg of TM per 30 g body weight daily for three consecutive days. BBN-containing water was provided to the mice ad libitum after the last TM injection. After 2 months, the mice were sacrificed, bladders harvested, and total RNA was prepared using the RNeasy Plus Mini Kit (Qiagen). RNA quality was evaluated using the Agilent 2100 Bioanalyzer system. Samples were hybridized to the Affymetrix GeneChip Mouse Exon 1.0 ST microarray chips. Three mice of each genotype were analyzed. After hybridization, expression values were normalized using the RMA function in the Partek Genomics Suite software. Differentially expressed genes were identified using ANOVA, genes showing a fold change greater or equal to 2 with P-value<0.01 were shortlisted for functional annotation analyses. Examination of overrepresented Gene Ontology Terms and Swiss-Prot (SP) and Protein Information Resource (PIR) Keywords (SP_PIR_KEYWORDS) was performed using DAVID[45] (http(colon)//david(dot)abcc (dot)ncifcrf(dot)gov/), in which enrichment in annotation terms was measured using a modified Fisher's Exact test. A p-value<0.05 was regarded as significant. Expression changes detected by microarray analysis were validated by verifying expression levels of several representative genes with quantitative RT-PCR.

Quantitative RT-PCR

Bladder samples were snap frozen in liquid nitrogen, homogenized with a mortar and pestle, and RNA extracted with the RNeasy Plus Mini kit (Qiagen). For quantitative RT-PCR of mRNA transcripts, first-strand cDNA was made using the SuperScript III First-Strand Synthesis SuperMix (Invitrogen 18080-400). Quantitative RT-PCR was performed using iQ SYBR Green Supermix (Bio-Rad 170-8880) and the Bio-Rad iCycler.

Human Bladder Cell Culture

Primary human bladder urothelial cells (ScienCell 4320) and bladder stromal fibroblasts (ScienCell 4330) were cultured in Urothelial Cell Medium (ScienCell 4321) and Fibroblast Medium (ScienCell 2301) respectively to subconfluency. Cells were then starved for 12 hours, followed by addition of Shh conditioned medium in the absence or in the presence of cyclopamine (3 uM, Toronto Research Chemicals), or treated with the Shh pathway agonist SAG (200 nM, Millipore) for 24 hours. In separate experiments, cells were treated with 20 ng/ml FK506 (Cayman Chemical) or DMSO for 12 hours. Following treatment, RNA was extracted using the Trizol reagent.

Pump Implantation

Alzet osmotic pumps (Alzet, no. 2004) were used to administer FK506 (Cayman Chemical) to mice at a dose of 0.05 mg per kg mouse body weight per day. Each pump was filled with 200 ul of FK506, then implanted subcutaneously into the back of each mouse, slightly posterior to the scapulae, and the incision closed with wound clips.

Statistical Analysis

Statistical analysis was performed using GraphPad Prism software v.5. All data are presented as mean±s.e.m., and two group comparisons were done with a two-tailed Student's t-test. A value of $P<0.05$ was taken as statistically significant.

REFERENCES

1. Taipale, J. & Beachy, P. A. The Hedgehog and Wnt signalling pathways in cancer. *Nature* 411, 349-354 (2001).
2. Shin, K. et al. Hedgehog/Wnt feedback supports regenerative proliferation of epithelial stem cells in bladder. *Nature* 472, 110-114 (2011).
3. Ahn, S. & Joyner, A. L. In vivo analysis of quiescent adult neural stem cells responding to Sonic hedgehog. *Nature* 437, 894-897 (2005).
4. Lai, K., Kaspar, B. K., Gage, F. H. & Schaffer, D. V. Sonic hedgehog regulates adult neural progenitor proliferation in vitro and in vivo. *Nat Neurosci* 6, 21-27 (2002).
5. Palma, V. Sonic hedgehog controls stem cell behavior in the postnatal and adult brain. *Development* 132, 335-344 (2005).
6. Shin, K. et al. Cellular origin of bladder neoplasia and tissue dynamics of its progression to invasive carcinoma. *Nature Cell Biology* (2013). Submitted.
7. Teglund, S. & Toftgård, R. Hedgehog beyond medulloblastoma and basal cell carcinoma. *Biochim. Biophys. Acta* 1805, 181-208 (2010).
8. Johnson, R. L. et al. Human Homolog of patched, a Candidate Gene for the Basal Cell Nevus Syndrome. *Science* 272, 1668-1671 (1996).
9. Hahn, H. et al. Mutations of the human homolog of *Drosophila* patched in the nevoid basal cell carcinoma syndrome. *Cell* 85, 841-851 (1996).
10. Yauch, R. L. et al. A paracrine requirement for hedgehog signalling in cancer. *Nature* 455, 406-410 (2008).
11. Olive, K. P. et al. Inhibition of Hedgehog Signaling Enhances Delivery of Chemotherapy in a Mouse Model of Pancreatic Cancer. *Science* 324, 1457-1461 (2009).
12. Roelink, H. et al. Floor plate and motor neuron induction by different concentrations of the amino-terminal cleavage product of sonic hedgehog autoproteolysis. *Cell* 81, 445-455 (1995).
13. Thievessen, I., Wolter, M., Prior, A., Seifert, H. H. & Schulz, W. A. Hedgehog signaling in normal urothelial cells and in urothelial carcinoma cell lines. *J. Cell. Physiol.* 203, 372-377 (2005).
14. Kimura, F. et al. Decrease of DNA methyltransferase 1 expression relative to cell proliferation in transitional cell carcinoma. *International Journal of Cancer* 104, 568-578 (2003).
15. Bryan, G. T. The pathogenesis of experimental bladder cancer. *Cancer Res* 37, 2813-2816 (1977).
16. Bryan, G. T. Pathogenesis of human urinary bladder cancer. *Environ. Health Perspect.* 49, 201-207 (1983).
17. Nagao, M., Suzuki, E., Yasuo, K., Yahagi, T. & Seino, Y. Mutagenicity of N-butyl-N-(4-hydroxybutyl)nitrosamine, a bladder carcinogen, and related compounds. *Cancer Res* 37, 399-407 (1977).
18. Bragdon, B. et al. Bone morphogenetic proteins: a critical review. *Cell. Signal.* 23, 609-620 (2011).
19. Mysorekar, I. U., Isaacson-Schmid, M., Walker, J. N., Mills, J. C. & Hultgren, S. J. Bone morphogenetic protein 4 signaling regulates epithelial renewal in the urinary tract in response to uropathogenic infection. *Cell Host Microbe* 5, 463-475 (2009).
20. Kawai, S. & Sugiura, T. Characterization of human bone morphogenetic protein (BMP)-4 and -7 gene promoters: activation of BMP promoters by Gli, a sonic hedgehog mediator. *Bone* 29, 54-61 (2001).
21. Roberts, D. J. et al. Sonic hedgehog is an endodermal signal inducing Bmp-4 and Hox genes during induction and regionalization of the chick hindgut. *Development* 121, 3163-3174 (1995).
22. Weaver, M., Yingling, J. M., Dunn, N. R., Bellusci, S. & Hogan, B. L. Bmp signaling regulates proximal-distal differentiation of endoderm in mouse lung development. dev.biologists.org
23. Schultheiss, T. M., Burch, J. B. & Lassar, A. B. A role for bone morphogenetic proteins in the induction of cardiac myogenesis. *Genes & Development* 11, 451-462 (1997).
24. Chen, J. K. Small molecule modulation of smoothened activity. *Proc Natl Acad Sci USA* 99, 14071-14076 (2002).
25. Cooper, M. K. Teratogen-Mediated Inhibition of Target Tissue Response to Shh Signaling. *Science* 280, 1603-1607 (1998).
26. Chen, J. K., Taipale, J., Cooper, M. K. & Beachy, P. A. Inhibition of Hedgehog signaling by direct binding of cyclopamine to smoothened. *Genes & Development* 16, 2743-2748 (2002).
27. Spiekerkoetter, E. et al. FK506 activates BMPR2, rescues endothelial dysfunction, and reverses pulmonary hypertension. *The Journal of Clinical Investigation* 123, 3600 (2013).
28. Samanta, J. & Kessler, J. A. Interactions between ID and OLIG proteins mediate the inhibitory effects of BMP4 on oligodendroglial differentiation. *Development* 131, 4131-4142 (2004).
29. Miyazono, K. & Miyazawa, K. Id: A Target of BMP Signaling. *Science Signaling* 2002, pe40 (2002).
30. Franzen, A. & Heldin, N.-E. BMP-7-Induced Cell Cycle Arrest of Anaplastic Thyroid Carcinoma Cells via p21 CIP1 and p27 KIP1. *Biochem Biophys Res Commun* 285, 773-781 (2001).
31. Chang, S. F. et al. BMP-4 Induction of Arrest and Differentiation of Osteoblast-Like Cells via p21CIP1 and p27KIP1 Regulation. *Molecular Endocrinology* 23, 1827-1838 (2009).
32. Sekulic, A. et al. Efficacy and Safety of Vismodegib in Advanced Basal-Cell Carcinoma. *New England Journal of Medicine* 366, 2171-2179 (2012).
33. Tang, J. Y. et al. Inhibiting the Hedgehog Pathway in Patients with the Basal-*Cell* Nevus Syndrome. *New England Journal of Medicine* 366, 2180-2188 (2012).
34. Ruch, J. M. & Kim, E. J. Hedgehog Signaling Pathway and Cancer Therapeutics: Progress to Date. *Drugs* 73, 613-623 (2013).
35. Rudin, C. et al. Treatment of medulloblastoma with hedgehog pathway inhibitor GDC-0449. *New England Journal of Medicine* 361, 1173 (2009).

36. Jamieson, C. et al. Phase 1 Dose-Escalation Study of PF-04449913, An Oral Hedgehog (Hh) Inhibitor, in Patients with Select Hematologic Malignancies. *ASH Annual Meeting and Exposition Abstract* (2011).
37. Kaye, S. B. et al. A Phase II, Randomized, Placebo-Controlled Study of Vismodegib as Maintenance Therapy in Patients with Ovarian Cancer in Second or Third Complete Remission. *Clinical Cancer Research* 18, 6509-6518 (2012).
38. Berlin, J. D. et al. A phase 2, randomized, double-blind, placebo-controlled study of Hedgehog pathway inhibitor (Hpi) GDC-0449 in patients with previously untreated metastatic colorectal cancer (MCRC). in *EMSO Meeting Abstract* (2010).
39. Infinity Reports Update from Phase 2 Study of Saridegib Plus Gemcitabine in Patients with Metastatic Pancreatic Cancer. http://phx.corporate-ir.net/phoenix.zhtml?c=121941 &p=irol-newsArticle&ID=1653550&highlight=
40. Wallemacq, P. E. & Reding, R. FK506 (tacrolimus), a novel immunosuppressant in organ transplantation: clinical, biomedical, and analytical aspects. *Clin. Chem.* 39, 2219-2228 (1993).
41. Sievert, K. D. et al. Economic aspects of bladder cancer: what are the benefits and costs? *World journal of urology* 27, 295-300 (2009).
42. Tian, H. et al. Hedgehog signaling is restricted to the stromal compartment during pancreatic carcinogenesis. *Proceedings of the National Academy of Sciences* 106, 4254-4259 (2009).
43. Kimura, H., Stephen, D., Joyner, A. & Curran, T. Gli1 is important for medulloblastoma formation in Ptc1+/- mice. *Oncogene* 24, 4026-4036 (2005).
44. Long, F., Zhang, X. M., Karp, S., Yang, Y. & Mcmahon, A. P. Genetic manipulation of hedgehog signaling in the endochondral skeleton reveals a direct role in the regulation of chondrocyte proliferation. *Development* 128, 5099-5108 (2001).
45. Huang, D. W. et al. DAVID Bioinformatics Resources: expanded annotation database and novel algorithms to better extract biology from large gene lists. *Nucleic Acids Research* 35, W169-W175 (2007).

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A method of treating a subject for bladder cancer, the method comprising administering a therapeutically effective amount of FK506 to the subject.
2. The method of claim 1, wherein the subject is human.
3. The method of claim 1, wherein the effective amount of an agent that activates BMP signaling is administered prophylactically to the subject.
4. The method of claim 3, wherein the prophylactic administration delays progression of a bladder cancer to an invasive cancer.
5. The method of claim 4, wherein the bladder cancer is a carcinoma and the invasive cancer is an invasive carcinoma.
6. The method of claim 1, wherein multiple cycles of the method of treatment are administered to said subject for a time period sufficient to effect at least a partial tumor response.
7. The method of claim 6, wherein the time period is at least 6 months.
8. The method of claim 7, wherein the time period is at least 12 months.
9. The method of claim 6, wherein a complete tumor response is effected.
10. The method of claim 1, wherein the FK506 is administered subcutaneously.
11. The method of claim 1, wherein low dose therapy is administered to the subject to avoid immunosuppression.
12. The method of claim 1, wherein the method further comprises administering a modulator of Hh signaling to the subject.
13. The method of claim 12, wherein the modulator of Hh signaling is a Hh antagonist.
14. The method of claim 12, wherein the modulator of Hh signaling is a Hh agonist.

* * * * *

UNITED STATES PATENT AND TRADEMARK OFFICE
CERTIFICATE OF CORRECTION

PATENT NO. : 9,814,703 B2
APPLICATION NO. : 15/147719
DATED : November 14, 2017
INVENTOR(S) : Philip A. Beachy et al.

Page 1 of 1

It is certified that error appears in the above-identified patent and that said Letters Patent is hereby corrected as shown below:

On the Title Page

PLEASE ADD
-- Related U.S. Application Data
(60) Provisional application No. 61/904,371, filed on November 14, 2013. --

Signed and Sealed this
Seventh Day of September, 2021

Drew Hirshfeld
*Performing the Functions and Duties of the*
*Under Secretary of Commerce for Intellectual Property and*
*Director of the United States Patent and Trademark Office*